United States Patent
Frid

(10) Patent No.: US 10,952,838 B2
(45) Date of Patent: Mar. 23, 2021

(54) STENT ASSEMBLY FOR THORACOABDOMINAL BIFURCATED ANEURYSM REPAIR

(71) Applicant: Cardiatis S.A., Brussels (BE)

(72) Inventor: Noureddine Frid, Beersel (BE)

(73) Assignee: Cardiatis S.A., Isnes (BE)

( * ) Notice: Subject to any disclaimer, the term of this patent is extended or adjusted under 35 U.S.C. 154(b) by 0 days.

(21) Appl. No.: 15/307,588

(22) PCT Filed: Mar. 5, 2015

(86) PCT No.: PCT/EP2015/054583
§ 371 (c)(1),
(2) Date: Oct. 28, 2016

(87) PCT Pub. No.: WO2015/132329
PCT Pub. Date: Sep. 11, 2015

(65) Prior Publication Data
US 2017/0100231 A1   Apr. 13, 2017

(30) Foreign Application Priority Data
Mar. 5, 2014 (EP) .................................. 14157770

(51) Int. Cl.
*A61F 2/06* (2013.01)
*A61F 2/852* (2013.01)
(Continued)

(52) U.S. Cl.
CPC ................ *A61F 2/06* (2013.01); *A61F 2/852* (2013.01); *A61F 2002/065* (2013.01);
(Continued)

(58) Field of Classification Search
CPC ............................................ A61F 2002/30228
See application file for complete search history.

(56) References Cited

U.S. PATENT DOCUMENTS 6,409,756 B1 * 6/2002 Murphy .................... A61F 2/07
623/1.16
6,666,883 B1 * 12/2003 Seguin ...................... A61F 2/07
623/1.15

(Continued)

FOREIGN PATENT DOCUMENTS

| WO | WO 97/12562 A1 | 4/1997 |
| WO | WO 01/54621 A1 | 8/2001 |
| WO | WO 2006/103641 A1 | 10/2006 |

OTHER PUBLICATIONS

Chiesa, Roberto, et al. "Spinal cord ischemia after elective, stent-graft repair of the thoracic aorta." *Journal of vascular surgery* 42.1 (2005): 11-17.

(Continued)

*Primary Examiner* — Jacqueline Woznicki
(74) *Attorney, Agent, or Firm* — Leydig, Voit & Mayer, Ltd.

(57) ABSTRACT

A multi-lumen stent assembly (100) for deployment in a bifurcated vessel. This assembly is made of a self-expandable main body component (200) and two lumen extensions (300), able to be inserted into one of the lumens of a double-barrelled portion (208) of the main body component (200). The main body component (200) has a proximal end (201) configured to be placed toward the heart and a distal end (202). The main body component (200) has a main body portion (203), a concaved portion (206), and a transition portion (205). The main body portion (203) has a cylindrical lumen (204) of constant diameter. The concaved portion (206) has a double-barrelled portion (208) having two lumens (211). A cross-section of the transition portion (205) evolving from a circular shape to an elliptical shape towards the transition portion (205), a larger diameter of this shape being in a central plane (CP).

11 Claims, 20 Drawing Sheets

(51) Int. Cl.
*A61F 2/82* (2013.01)
*A61F 2/30* (2006.01)

(52) U.S. Cl.
CPC .............. *A61F 2002/30228* (2013.01); *A61F 2002/823* (2013.01); *A61F 2002/826* (2013.01); *A61F 2230/001* (2013.01); *A61F 2230/0006* (2013.01); *A61F 2230/0008* (2013.01); *A61F 2250/0039* (2013.01); *A61F 2250/0063* (2013.01)

(56) References Cited

U.S. PATENT DOCUMENTS

| | | | | |
|---|---|---|---|---|
| 2003/0204242 | A1* | 10/2003 | Zarins | A61F 2/07 623/1.16 |
| 2004/0138736 | A1* | 7/2004 | Obara | A61B 17/12022 623/1.16 |
| 2005/0043784 | A1 | 2/2005 | Yampolsky et al. | |
| 2005/0240261 | A1 | 10/2005 | Rakos et al. | |
| 2006/0095119 | A1* | 5/2006 | Bolduc | A61B 17/064 623/1.36 |
| 2007/0162104 | A1* | 7/2007 | Frid | A61F 2/856 623/1.15 |
| 2013/0103163 | A1* | 4/2013 | Krimsky | A61F 2/04 623/23.65 |
| 2013/0289701 | A1* | 10/2013 | Coghlan | A61F 2/07 623/1.13 |
| 2013/0289702 | A1* | 10/2013 | Coghlan | A61F 2/07 623/1.13 |
| 2014/0296963 | A1* | 10/2014 | Akingba | A61F 2/07 623/1.13 |
| 2017/0281375 | A1* | 10/2017 | Longo | A61F 2/848 |

OTHER PUBLICATIONS

De la Cruz, Kim I., et al. "Thoracoabdominal aortic aneurysm repair with a branched graft." *Annals of cardiothoracic surgery* 1.3 (2012): 381-393.

Hiratzka, Loren F., et al. "2010 ACCF/AHA/AATS/ACR/ASA/SCA/SCAI/SIR/STS/SVM guidelines for the diagnosis and management of patients with thoracic aortic disease." *Journal of the American College of Cardiology* 55.14 (2010).

International Search Report and Written Opinion for Application No. PCT/EP2015/054583 dated Sep. 11, 2015.

* cited by examiner

Fig. 5
(Prior Art)
Fig. 6
(Prior Art)
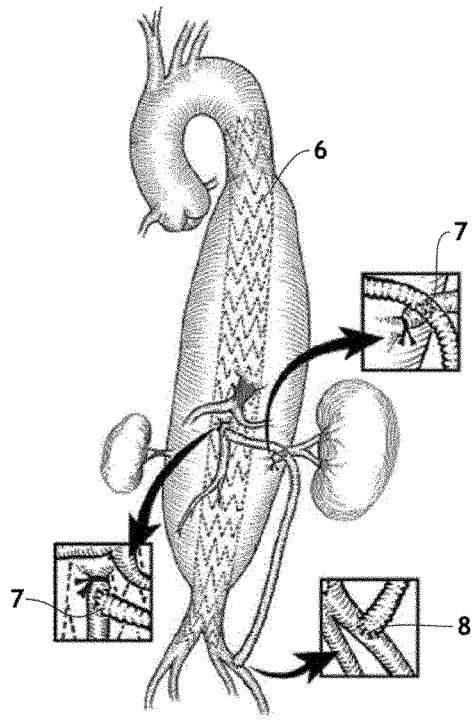
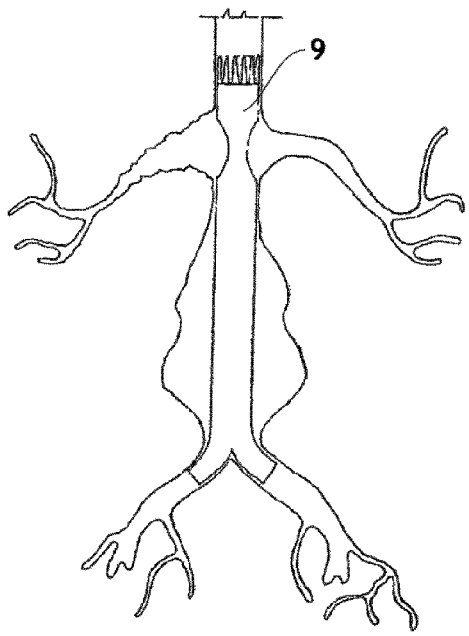
Fig. 7
Fig. 8
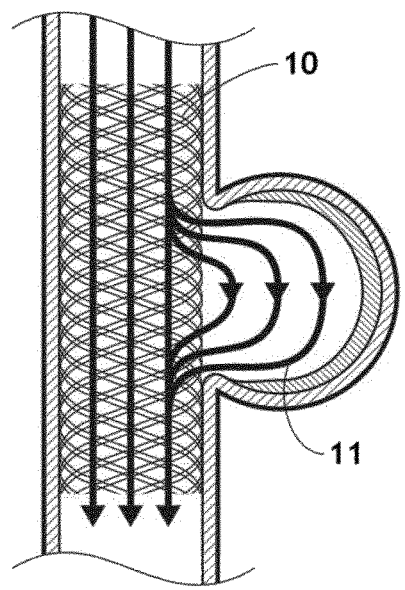
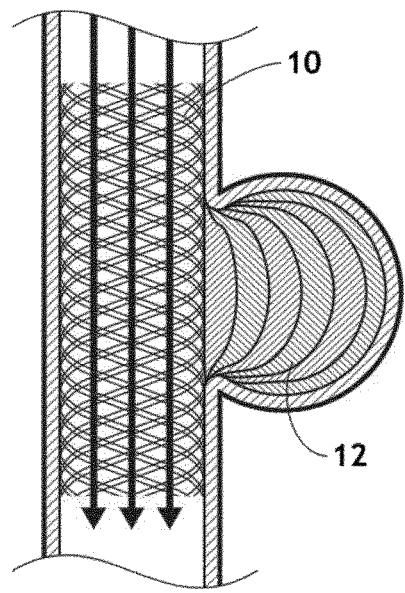

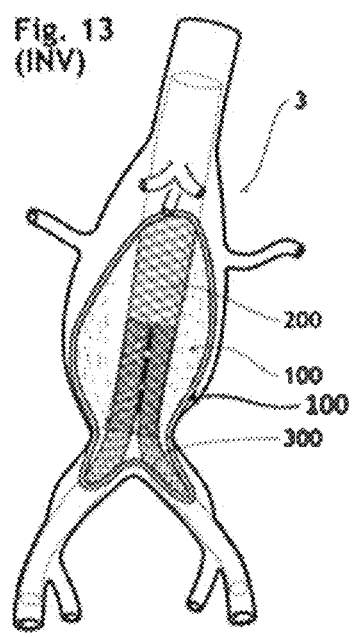
Fig. 13 (INV)
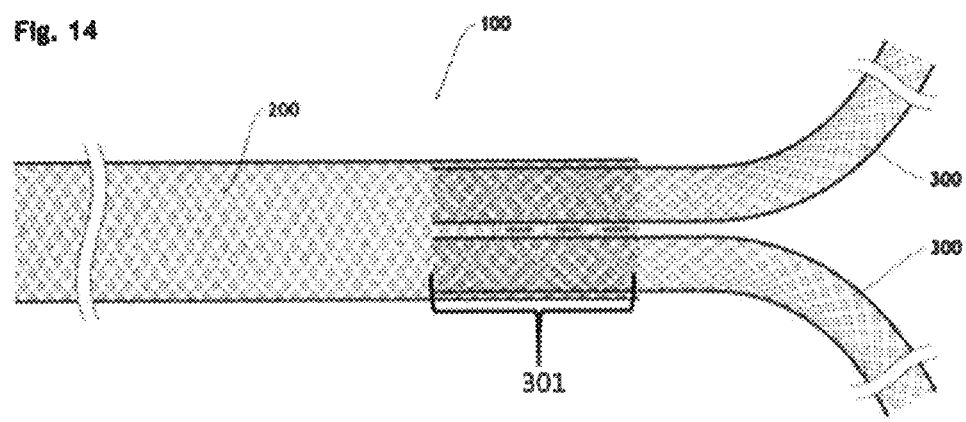
Fig. 14
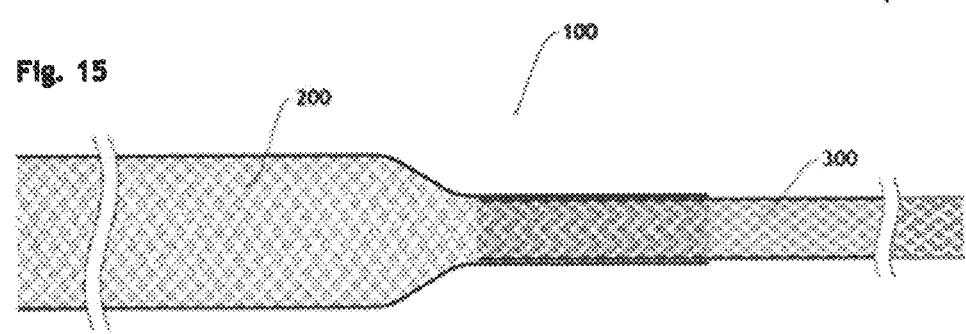
Fig. 15

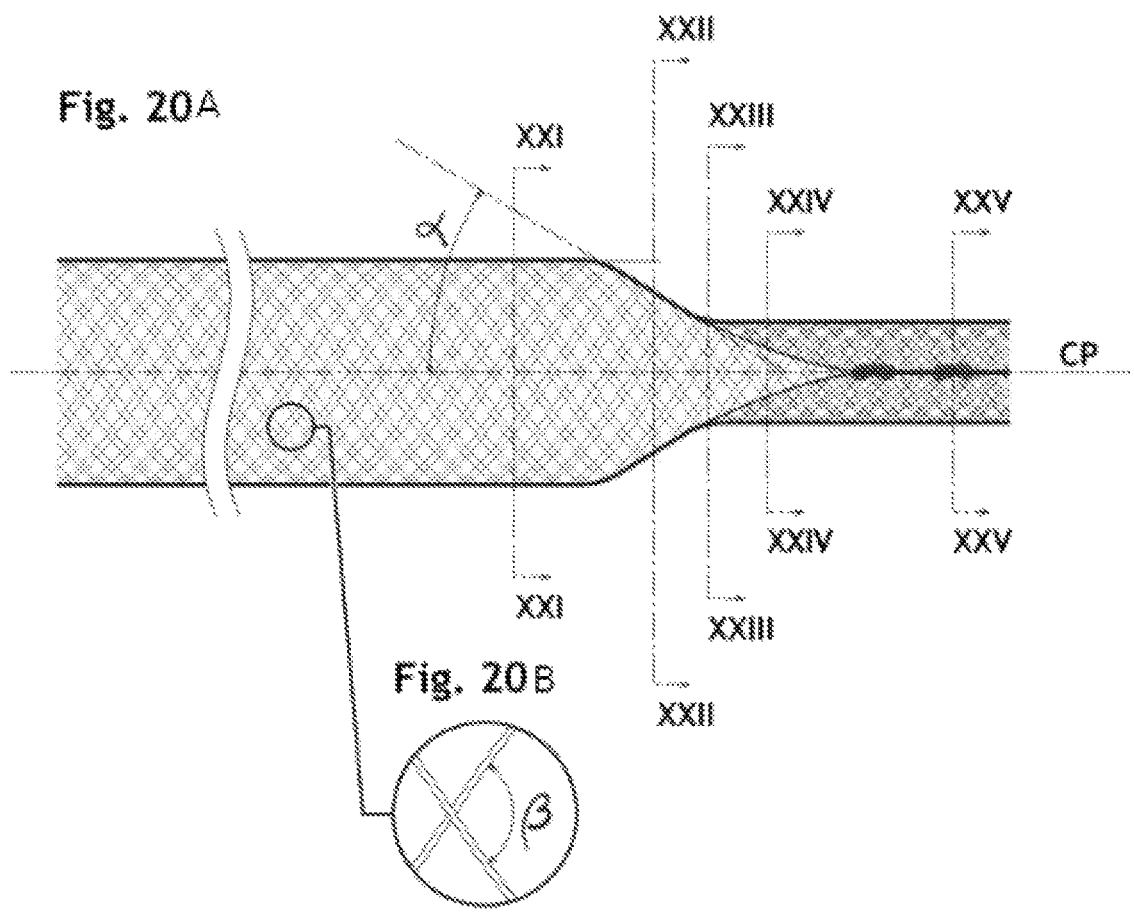
Fig. 20A
Fig. 20B
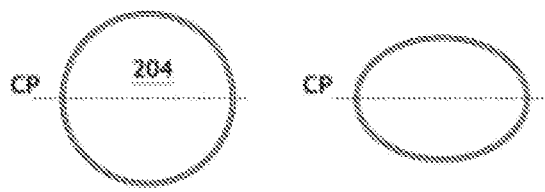
Fig. 21  Fig. 22  Fig. 23
Fig. 24
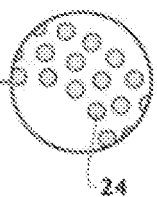
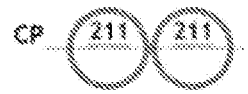
Fig. 25  Fig. 26

(INV)

(INV)

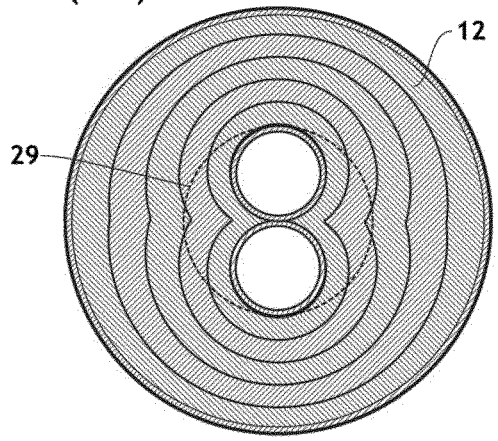
Fig. 36 (INV)
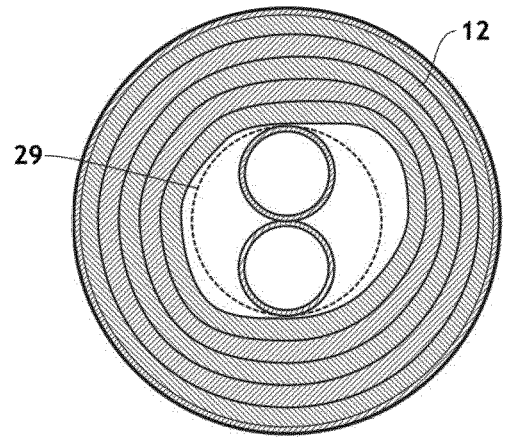
Fig. 37
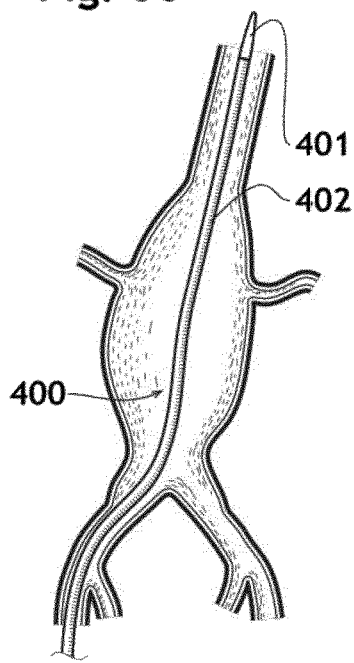
Fig. 38
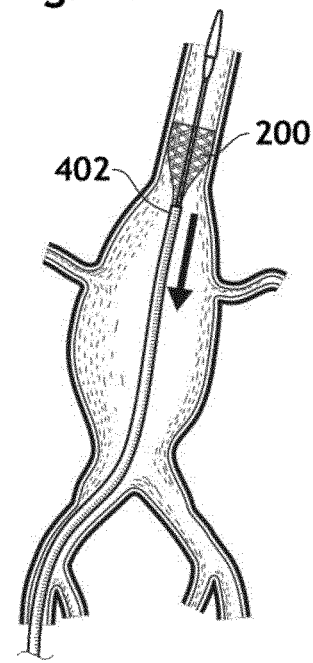
Fig. 39
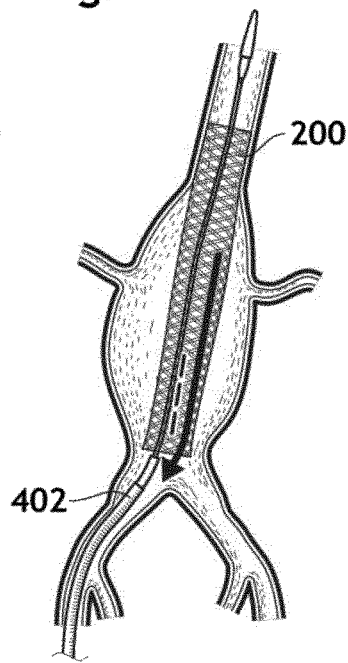
Fig. 40

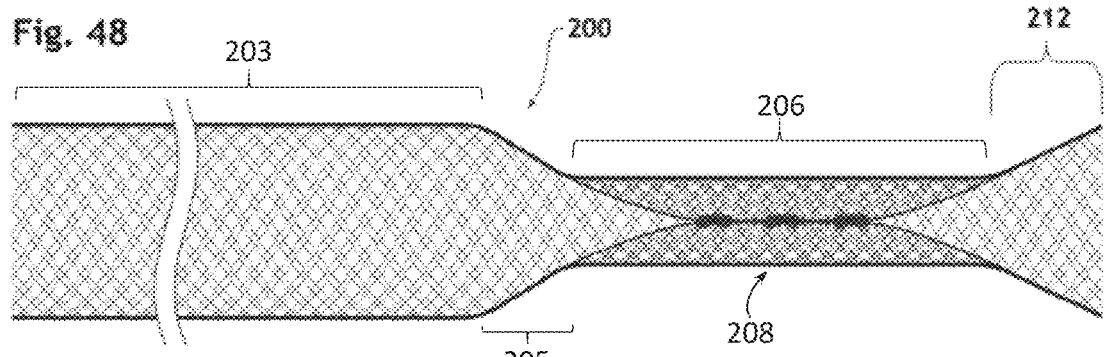
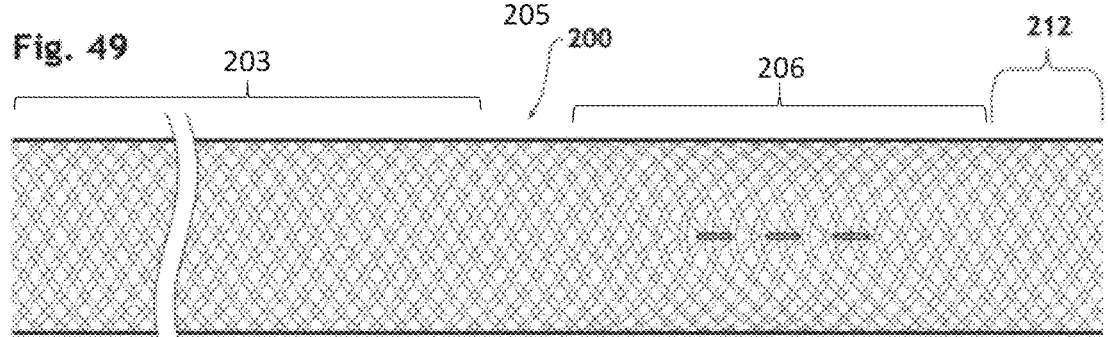
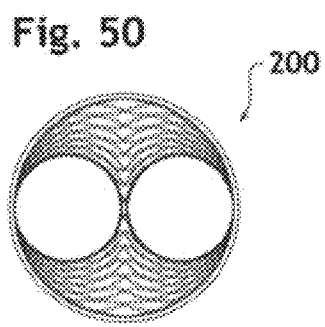 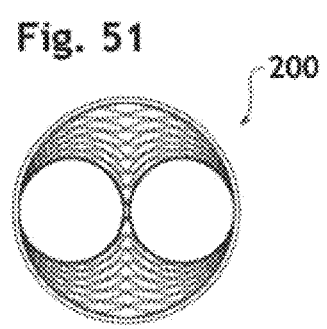
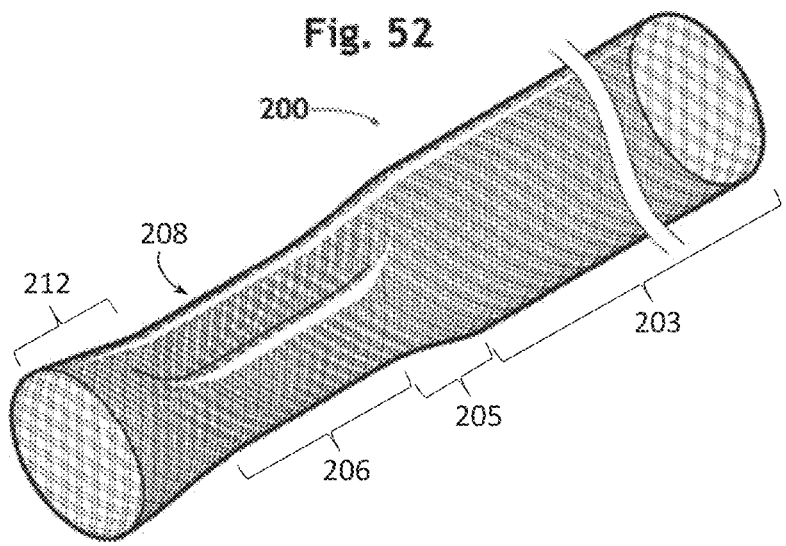

 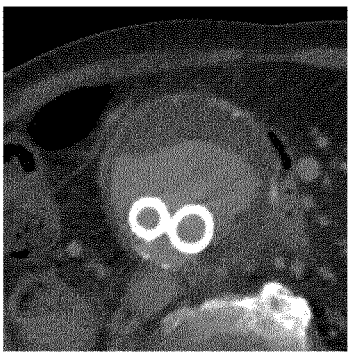 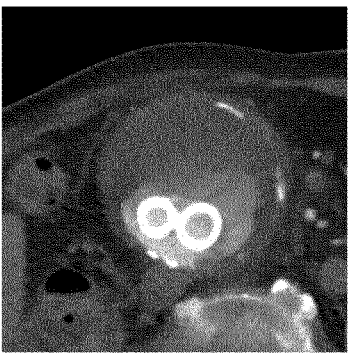
*Fig. 66*     *Fig. 67*     *Fig. 68*
*Fig. 69*

STENT ASSEMBLY FOR THORACOABDOMINAL BIFURCATED ANEURYSM REPAIR

TECHNICAL FIELD

The present invention relates to implantable medical devices in a bifurcated vessel, in particular, stent assemblies suitable for treatment of a thoracoabdominal bifurcated aneurysm (TABA), namely an enlarged thoracoabdominal aneurysm involving the aortic bifurcation or at least one of iliac arteries. The present invention also relates to methods for manufacturing said medical devices.

BACKGROUND OF THE INVENTION

Aneurysm is a localized pathological dilation of the wall of a vessel, which is formed as a results of degenerative processes of the arterial wall being subjected to exceptionally high levels of shear stress. Shear stress is the drag force of blood as the blood flows over a vessel wall. A combination of this drag force and genetic predisposition can initiate an aneurysm. Once aneurysm is formed, abnormal hemodynamic patterns, such as turbulent flow, which amplifies oscillatory shear stress acting on one area of the wall as a peak of wall shear stress (PWSS) (FIGS. 1 and 2). Area of the PWSS may weaken the wall and leads eventually to rupture and death.

Aneurysm of the aorta primarily occurs in the abdominal region, usually in the infrarenal area between the renal arteries and the aortic-iliac bifurcation. Aneurysm can also occur in the thoracic region between the artic arch and renal arteries.

Thoracoabdominal bifurcated aneurysm 1 (TABA) results from continuous dilation of the descending thoracic aorta extending into the abdominal aorta involving iliac arteries 2 (FIG. 3). It may be identified incidentally or due to the present with symptoms secondary to aneurysm expansion. Generally, the mortality of this type of untreated aneurysm is high. Present treatments for the thoracoabdominal aneurysm is challenging by the presence of visceral 3 and renal 4 branches. Currently, the available techniques of treatments, as open surgery or fenestrated stent-graft, are not the optimal solution due to the high rate of complications.

Generally, open surgical repair of thoracoabdominal bifurcated aneurysm (TABA) is considered as the first option for those who are medically fit. Kim I. de la Cruz, et.al describes in an article, "Thoracoabdominal aortic aneurysm repair with a branched graft", *Ann Cardiotborac Surg* 2012; 1(3): 381-393, an operative method consisting of proximal and distal control of the aneurysm, followed by its incision to simultaneously expose the origin of all four major intra-abdominal arteries and replacement of the diseased or damaged section of vessel with a vessel graft 5 including anastomosis of major intra-abdominal arteries, which is usually unsupported impermeable woven tube. The vessel graft 5 is then permanently attached and sealed to ends of the native vessel by suture (FIG. 4). Despite of careful case selection, high mortality rates with such conventional surgical repair are reported because of the highly traumatic operation including both of laparotomy and thoracotomy.

Endovascular prosthesis 6 is often taken as alternative option for patients who are unfit to withstand either laparotomy or thoracotomy. Typically, these prosthesis for aortic aneurysms are delivered collapsed in a catheter through the femoral artery. These prostheses are usually designed with an impermeable fabric material co-attached with a metallic frame (i.e., stent-graft), which expands or is expanded to contact the internal diameter of vessel. However, an open surgery is still required for a debranching 7 and bypass 8 operation of arteries prior to the endovascular grafting in order to secure a blood flow into main arteries such as renal and visceral and to prevent a reflux therefrom, as described by Hiratzka et al in "2010 ACCF/AHA/ACR/ASA/SCA/SCAI/SIR/STS/SVM Guidelines for the Diagnosis and Management of Patients With Thoracic Aortic Disease", *Circulation* 2010; 121 e266-e369 (FIG. 5).

WO97/12562 discloses a branching endoluminal stent-graft having Y-connector module including two branch lumens. Two branching prosthetic modules engages the branch lumens so as to separates the blood flow for the iliac arteries. Since the described stent-graft includes liners which are impermeable, it is not possible to use it for treating an aortic aneurysm involving visceral 3 and renal 4 branches.

Fenestrated and branched stent-grafts have been introduced to overcome the problems associated with the endovascular grafting involving the open debranching and bypass operation, and to offer a potentially less invasive method. For example, United States Published Patent Application 2010/0023110 discloses a fenestrated stent-graft 9 used in conjunction with flaring stent-grafts as branches (FIG. 6). By positioning the fenestrations or branches of the stent-graft 9 at the front of the corresponding branches inlets, the open surgery can be avoided. However, highly skilled operators are required for the adequate positioning and deployment. Furthermore, such fenestrated and branched stent-grafts must be custom-made to fit each patient's anatomy. Additionally, it is known that spinal cord ischemia caused by incidentally covering intercostal arteries with a stent-graft can lead to paraplegia and expose the patient to X-ray for long period of 90 minutes. The incidence of both immediate and delayed paraplegia in patients undergoing endovascular can be as high as 12% of cases compared with 2% to 21% after open repair as reported by Chiesa et al in "Spinal cord ischemia after elective stent-graft repair of the thoracic aorta", (*Journal of Vascular Surgery*, vol. 42, N.1, July 2005).

A new type of aneurysm repair system with a multilayer braided stent 10 (MBS) as described in U.S. Pat. Nos. 7,588,597 and 8,192,484 was recently introduced by Frid et al. The repair system consists of a bare self-expandable metal stent in a straight configuration devoid of any impermeable cover layer. MBS consists of a plurality of interconnected layers (i.e., multilayer structure) formed by braiding a plurality of wires. Each of these layers is interlaced to form a lattice and provides a wall of the MBS with an optimized porosity. Instead of mechanically/physically keeping out the blood flow from the aneurysm, MBS 10 lets the blood flow into the aneurysm sac through its multilayer structure, converts an undesired damaging turbulence in the aneurysmal sac into a smooth laminar flow 11 (FIG. 7), and results in excluding the aneurysm by forming a protecting organized thrombus 12, known as layers of Zhan (FIG. 8), while keeping the branches and collaterals patent. Thanks to the permeable multilayer structure of MBS, the repair system does require neither open debranching and bypass procedure nor custom-made fenestrated/branched configuration for maintaining a blood flow in branches located within or near aneurysm.

However, the conventional straight multilayer braided stent (MBS) described in U.S. Pat. No. 7,588,597 or 8,192,484 is not ideal to treat the thoracoabdominal bifurcated aneurysm 1 (TABA). For example, two straight MBS having different diameters may be used for treatment of TABA. A first straight MBS 13 having a large diameter may be placed from the aortic to one iliac through the aortic-iliac bifurcation and a second straight MBS 14 having small diameter from the aortic-iliac bifurcation to the other iliac as shown in FIG. 9. However, since an adequate landing zone at the beginning of the small MBS 14 is missing, undesired migration of the small MBS 14 may occur after implantation. Furthermore, the gap may occur between the first straight MBS 13 and the small MBS 14, resulting in lack of sealing.

There is another possible use of the conventional straight MBS which consists of a main straight MBS 15 and two small MBSs 16 positioning inside the main MBS, namely kissing technique (FIGS. 10 to 12). This configuration causes undesired turbulent flow 17 as shown in FIG. 11.

Accordingly, there is a need for new design of prosthesis, systems and methods that manufacture the prosthesis, the prosthesis being able to exclude a thoracoabdominal bifurcated aneurysm (TABA) while maintaining the blood flow of branches and collaterals located around and within the aneurysm.

SUMMARY OF THE INVENTION

The object of the invention is to provide a prosthesis assembly for treatment of enlarged thoracoabdominal aortic aneurysms involving the aortic-iliac bifurcation and/or an iliac artery, namely thoracoabdominal bifurcated aneurysm (TABA), which is capable to exclude the aneurysm while maintaining the blood flow without any traumatic open surgery.

The subject of the present invention is defined in the appended independent claims. Preferred embodiments are defined in the dependent claims.

A subject of the present invention is a multi-lumen stent assembly suitable for deployment in a bifurcated vessel comprising a main vessel and at least two branches. Said assembly comprises a self-expandable main body component capable of expanding from a radially compressed state in a delivery configuration to a radially expanded state, and two lumen extensions.

The main body component has a proximal end configured to extend toward away from the branches of the bifurcated vessel (i.e. to be placed toward the heart) and a distal end configured to extend towards the branches of the bifurcated vessel (i.e., to be placed toward away from the heart), and it extends along an axis. The main body component is formed of a multilayer braiding with a plurality of filaments and is devoid of any cover layer. Preferably the main body component is formed of an interconnected multilayer braiding, more preferably it is formed of an interlaced multilayer braiding. The main body component comprises a main body portion at the proximal end of main body component, a concaved portion towards the distal end of main body component, and a transition portion extending between the distal end of the main body portion and a proximal end of the concaved portion. The main body portion comprises a lumen in a cylindrical form with a circular cross-section and a constant diameter. The concaved portion comprises a double-barrelled portion. Middle lines of the concaved portion are concaved along the longitudinal axis of the main body component and defines two opposing ridges within an interior of the concaved portion. Each ridge partially contacts the other ridge. The two opposing ridges defines two lumens of the double-barrelled portion. Each of the two lumens extending along an axis. The axes of the two lumens defines a central plane (CP) which also comprises the axis of the main body component. A cross-section of the transition portion evolves from a circular shape towards the proximal end of the transition portion to an elliptical shape towards the distal end of the transition portion. A larger diameter of this elliptical shape is in the central plane (CP). An intersection of the wall of the transition portion defined by a plane comprising the axis of the main body component and normal to the central plane (CP) defines an angle $\alpha$ with respect to the central plane (CP). Said angle $\alpha$ is comprised between at least 10° and at most 55° when the stent assembly is in a deployed state.

The lumen extension comprises a tip portion able to be inserted into one of the lumens of the double-barrelled portion from the distal end of the main body component.

When the stent assembly is in a deployed state, the porosity of the main body portion is preferably at least 50% and at most 75%, preferably at least 60% and at greatest 70%, and the porosity of the double-barrelled portion is preferably less than the porosity of the main body portion.

According to a preferable embodiment, the concaved portion further comprises a distal portion between the double-barrelled portion and the distal end of the main body component, wherein the distance between the two ridges increases toward the distal end. Preferably, the distal portion of the concaved portion has a diverging cone-shape.

Advantageously, the angle $\alpha$ defined by the intersection of the wall of the transition portion with respect to the central plane (CP) is at least 15°, preferably at least 20°, and at most 55°, preferably at most 45°, more preferably at most 35°, even more preferably at most 25° with respect to the central plane (CP).

When the stent assembly is in a deployed state, an angle ($\beta$) formed between crossing braided filaments of the double-barrelled portion is preferably greater than 95°, more preferably at least 100° and at greatest 150°.

According to still another preferable embodiment, the lumen extension is a stent devoid of any impermeable layer, preferably, formed of a multilayer braided framework made of a plurality of filaments. Advantageously, the multilayer braided framework comprises a plurality of interconnected layers and each layer is interlaced to form a lattice. Preferably, the multilayer braided framework has, in its deployed state, a configuration of that an outermost layer of the framework applies against the wall of the body lumen and the other layers extending substantially along cylindrical surfaces distinct from the outermost layer. Advantageously, the external diameter of lumen extension is at least 10%, preferably at least 13%, and at most 50%, preferably at most 20% greater than the inner diameter of the double-barrelled portion of the main body component in their fully expanded states.

Another subject of the present invention is a method for manufacturing a main body component for a prosthesis assembly for deployment into a bifurcated vessel comprising a main vessel and at least two branches, preferably within an aorta and iliac arteries. Said method comprises the following steps:

a) providing a mandrel having at least one main portion comprising a cylindrical form and at least two bars connecting to a distal end of the main portion, the two bars being in a cylindrical form and disposed parallel to each other having smaller diameter than the diameter of the cylindrical portion, a linear space being disposed between the two bars along the longitudinal axis of the mandrel;

b) providing metal filaments selected from a group of cobalt alloy, titanium, and titanium alloy;
c) making a bundle of the metal filaments at an end of the mandrel and fixing the bundle with a fixing means;
d) forming a braided framework around the mandrel with the provided metal filaments, the braided framework having at least one cylindrical portion and at least one flattened portion having an oval cross-section;
e) making a bundle of the metal filaments and fixing with a fixing means at the other end of the mandrel;
f) putting the mandrel and surrounding braided framework into a plastic tube or sac;
g) subjecting the mandrel and surrounding braided framework in the plastic tube or sac to an external, preferably hydraulic, pressure so as to create a concaved shape in the flatten portion along the linear space of the mandrel;
h) subjecting the concaved framework to a thermal treatment so as to memorize the concaved shape;
i) cutting off both ends of the thermal treated framework.

Another subject of the present invention relates to the multi-lumen stent assembly indicated above for use of treating a thoracoabdominal bifurcated aneurysm (TABA), i.e., an enlarged thoracoabdominal aneurysm involving the aortic-iliac bifurcation and/or an iliac artery, where an adequate landing zone around the bifurcation is not available for conventional endovascular prosthesis.

BRIEF DESCRIPTION OF THE FIGURES

FIG. 5 is a partial, cross-section view of a thoracoabdominal aortic aneurysm, showing a stent-graft placed, occluded main arteries, and a bypass (according to the prior art).

FIG. 6 is a partial, cross-section view of an abdominal aortic aneurysm extending into the renal arteries, showing a fenestrated stent-graft (according to the prior art) placed in the aorta such that fenestrations are aligned with the renal arteries.

FIG. 7 shows a laminated blood flow formed in an aneurysm after implantation of a multilayer braided stent.

FIG. 8 shows an organized thrombus formed in an aneurysm after implantation of a multilayer braided stent.

FIG. 13 is a partially cutaway elevation view of a thoracoabdominal bifurcated aneurysm (TABA), showing a completely deployed multi-lumen stent assembly according to present invention through the TABA.

FIG. 14 is an elevation view of an embodiment of a multi-lumen stent assembly according to the present invention in fully expanded state.

FIG. 15 is a side view of the multi-lumen stent assembly shown in FIG. 14.

FIG. 20A is a side view of the main body component shown in FIG. 16.

FIG. 20B is a magnified view of a portion of the main body component illustrated in FIG. 20A.

FIGS. 21 and 22 are a schematic cross-section of the main body component shown in FIG. 16 according to cutting planes XXI-XXI and XXII-XXII of FIG. 20A, respectively.

FIG. 23A is a schematic cross-section of the main body component shown in FIG. 16 according to cutting plane XXIII-XXIII of FIG. 20A.

FIG. 23B is a schematic magnified view of a portion of the cross-section shown in FIG. 23A.

FIGS. 24 and 25 are a schematic cross-section of the main body component shown in FIG. 16 according to cutting planes XXIV-XXIV and XXV-XXV of FIG. 20A, respectively.

FIG. 26 is a schematic drawing showing how to braid a plurality of plies to obtain an interconnected multilayer configuration of an embodiment of a main body component and a lumen extension according to the present invention.

FIG. 36 is a section view of the completely thrombosed aneurysm and the stent assembly shown in FIG. 34 according to a cutting plane XXXVI-XXXVI of FIG. 34.

FIG. 37 is a section view of the partially thrombosed and the stent assembly shown in FIG. 35 according to a cutting plane XXXVII-XXXVII of FIG. 35.

FIGS. 38 to 42 shows a series of deployment steps of the prosthesis according to the present invention.

FIG. 48 is a side view of a preferred embodiment of the main body component according to the present invention in fully expanded state.

FIG. 49 is an elevation view of the main body component shown in FIG. 48.

FIG. 50 is a plan view of the main body component shown in FIG. 48.

FIG. 51 is a bottom view of the main body component shown in FIG. 48.

FIG. 52 is a perspective view of the main body component shown in FIG. 48.

FIGS. 66 to 68 are CT-scan images of a patient respectively before implantation, 1 month and 2 months after implantation of the multi-lumen stent assembly according to the present invention.

FIG. 69 is an X-ray image of patient with the multi-lumen stent assembly according to the present invention.

DETAILED DESCRIPTION OF THE INVENTION

Figure 1:
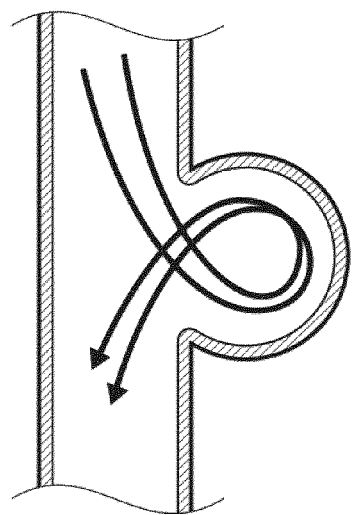
FIG. 1 shows a blood flow direction within an aneurysm.
Figure 2:
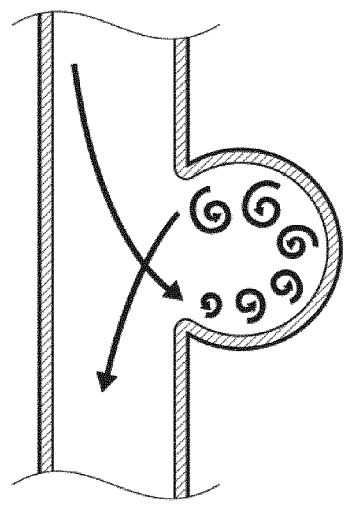
FIG. 2 shows an abnormal hemodynamic pattern formed in an aneurysm.
Figure 3:
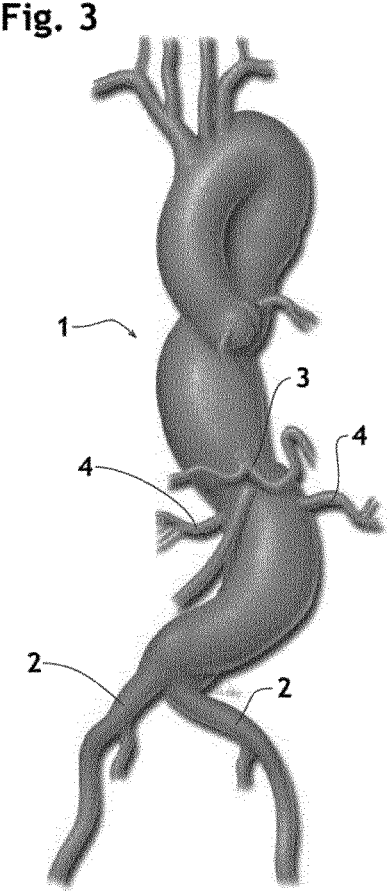
FIG. 3 shows an aorta and iliac arteries with a thoracoabdominal bifurcated aneurysm (TABA).
Figure 4:
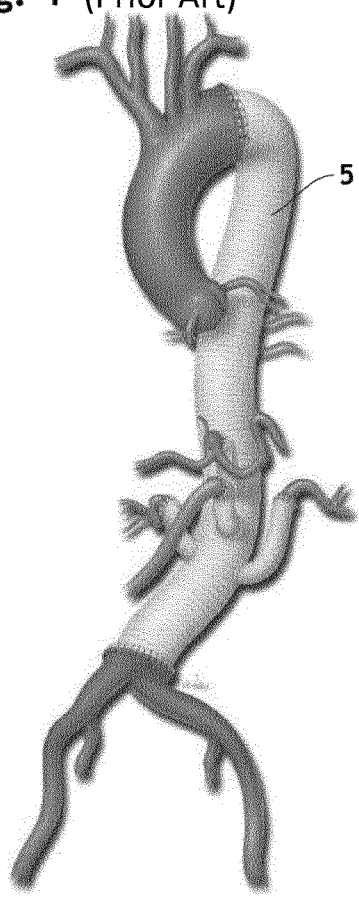
FIG. 4 shows an aorta and iliac arteries partially replaced with artificial grafts by open surgery repair (according to the prior art).
Figure 9:
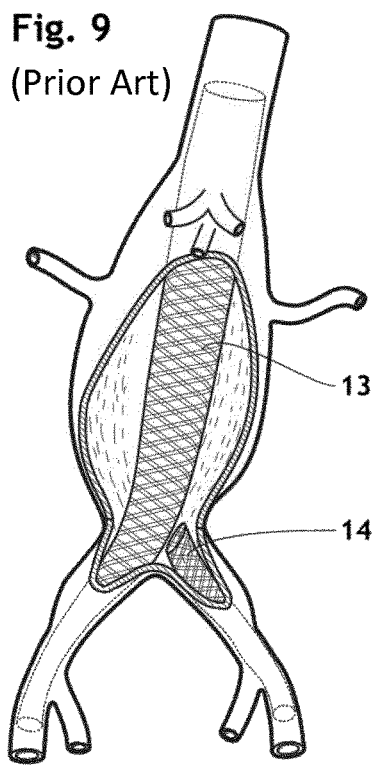
FIG. 9 is a partially cutaway elevation view of a thoracoabdominal bifurcated aneurysm (TABA) and conventional (i.e. according to the prior art) straight multilayer braided stents (MBS) deployed therein.
Figure 12:
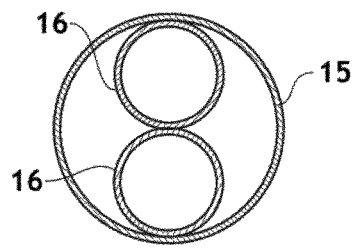
FIG. 12 is a section view of the distal end of the conventional MBS shown in FIGS. 10 and 11 according to a cutting plane XII-XII of FIG. 11.
Figure 10:
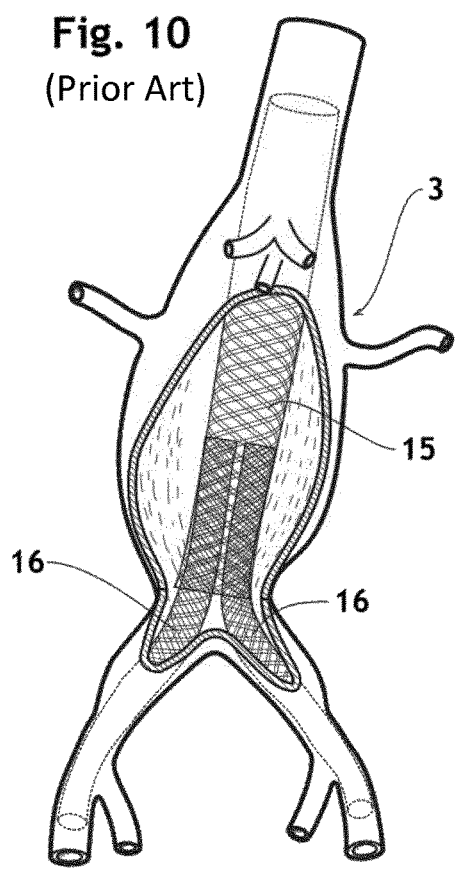
FIG. 10 is an elevation view of conventional (i.e. according to the prior art) straight multilayer braided stents (MBS) deployed in a configuration of kissing through a thoracoabdominal bifurcated aneurysm (TABA).
Figure 11:
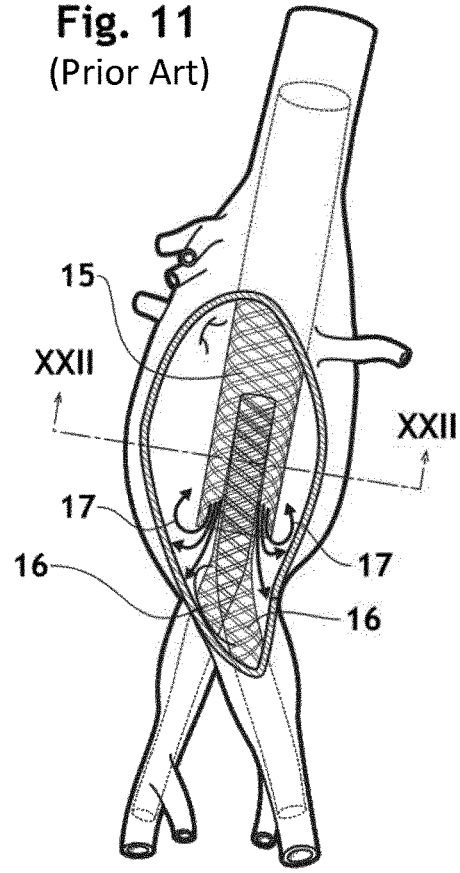
FIG. 11 is a perspective view of the conventional MBS shown in FIG. 10.
Figure 16:
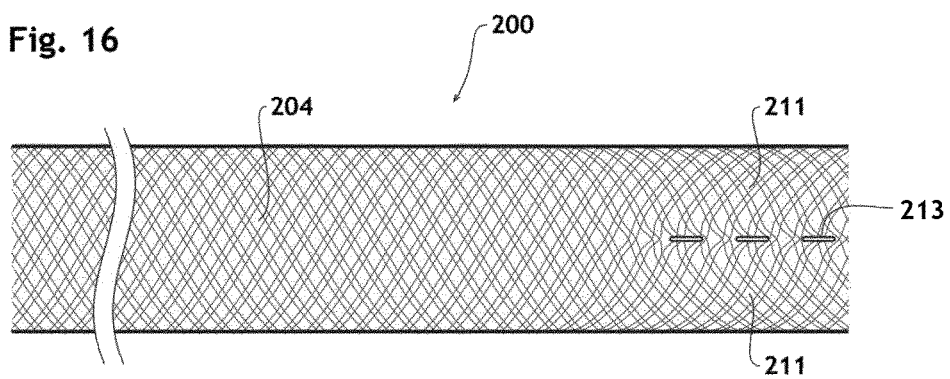
FIG. 16 is an elevation view of an embodiment of a main body component according to the present invention in fully expanded state.
Figure 17:
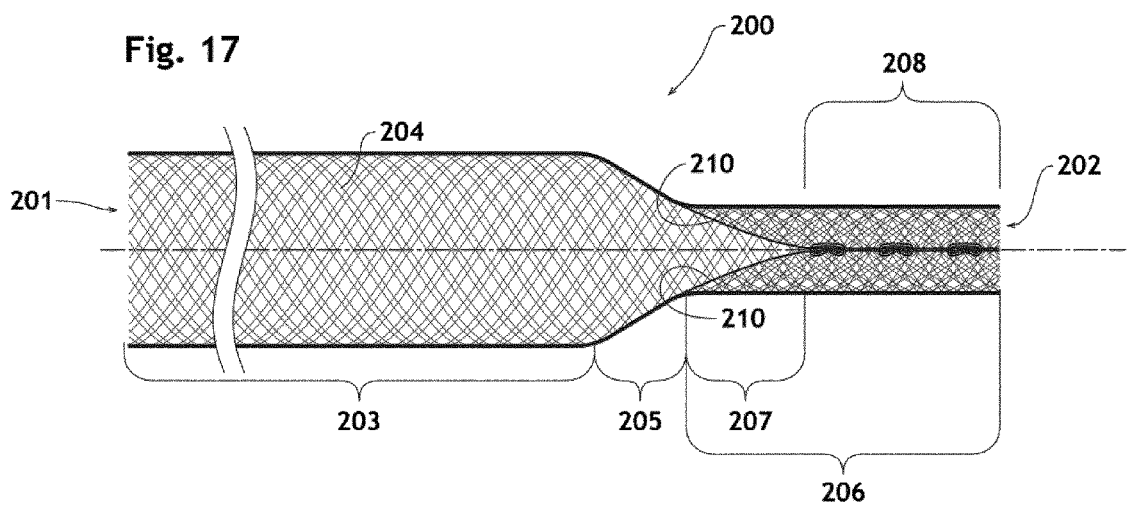
FIG. 17 is a side views of the main body component shown in FIG. 16.
Figure 18:
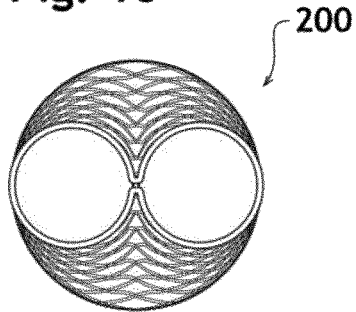
FIG. 18 is a bottom view of the main body component shown in FIG. 16.
Figure 19:
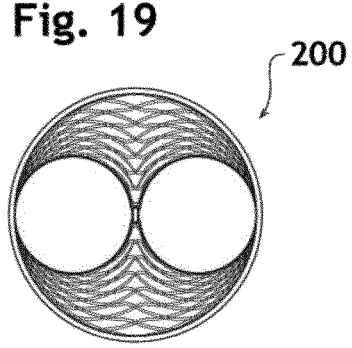
FIG. 19 is a plan view of the main body component shown in FIG. 16.
Figure 27:
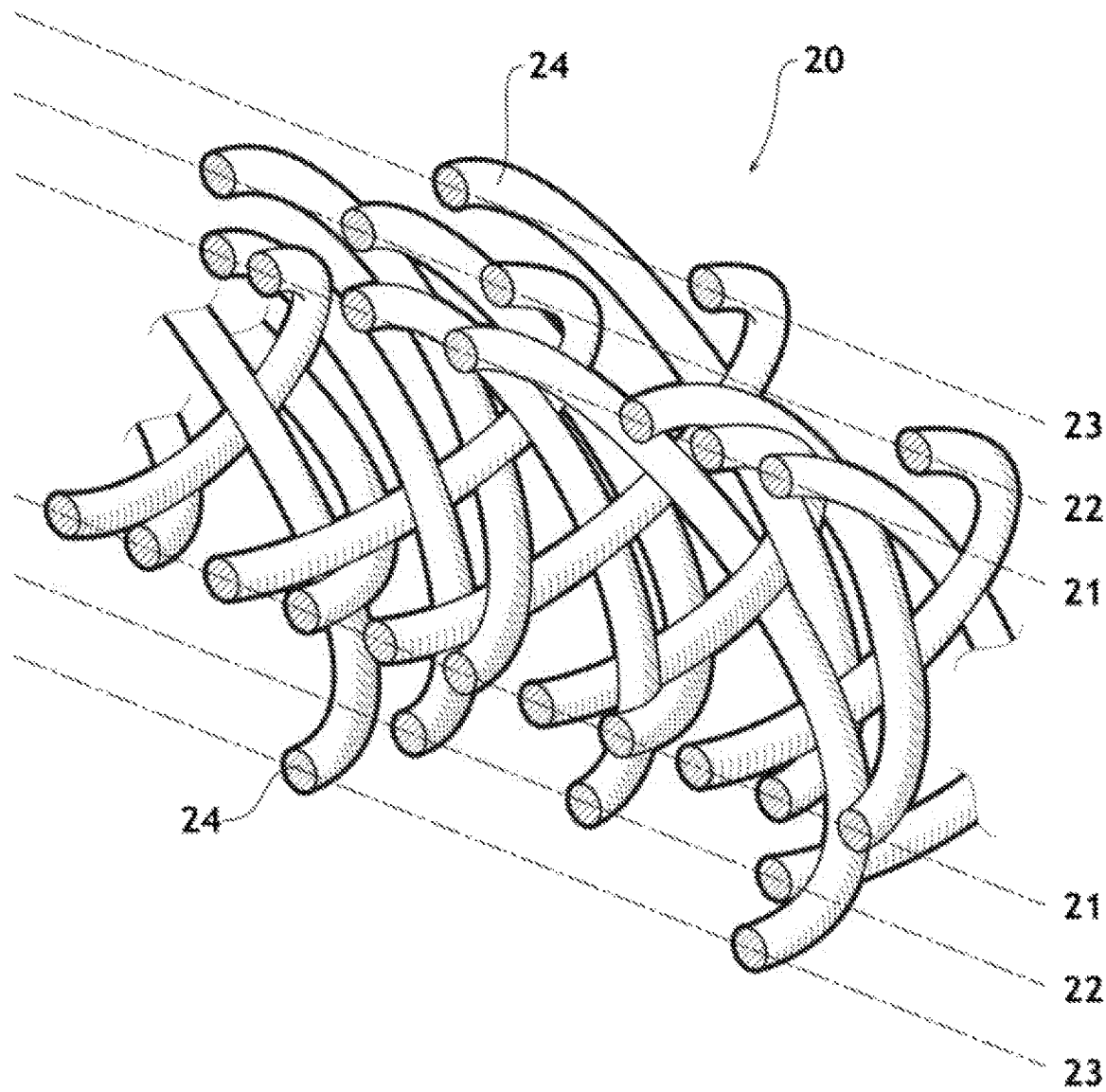

FIG. 13 depicts a multi-lumen prostheses assembly 100 according to the present invention completely deployed (in a deployed state) in an enlarged thoracoabdominal bifurcated aneurysm (TABA) involving iliac arteries.

As shown in FIGS. 14 and 15, the multi-lumen stent assembly 100 comprises a self-expandable main body component 200 and two lumen extensions 300. The main body component 200 is capable of expanding from a radially compressed state in a delivery configuration to a radially expanded state. The term of "deployed configuration" or "deployed state" refers to respectively a configuration or state being radially expanded within the delivered location such as a body lumen. The terms of "fully expanded configuration" or "fully expanded state" refers to respectively a configuration or state exerted by a self-expanding property of a self-expanding object (e.g., main body component 200 and lumen extension 300). Each lumen extension comprises a tip portion 301 which is able to be inserted into the distal end of the main body component 200.

As shown in FIGS. 16 to 25, the main body component 200 has a proximal end 201 to be placed toward the heart and a distal end 202 to be placed toward away from the heart. The main body component 200 extends along an axis. The main body component 200 comprises a main body portion 203 at its proximal end 201. The main body portion 203 comprises a lumen 204 in a cylindrical form with a circular cross-section and a constant diameter.

The main body component 200 further comprises a concaved portion 206 towards the distal end 202 of main body component 200. The concaved portion 206 comprises a double-barrelled portion 208, middle lines of which is concaved along the longitudinal axis of the main body component 200 and defines two opposing ridges 210 within an interior of the concaved portion 206. Each ridge 210 partially contacts the other ridge 210 and the two opposing ridges 210 define two lumens 211 of the double-barrelled portion 208. Each of the two lumens 211 of the double-barrelled portion 208 extends along an axis and the axes of the two lumens 211 define a central plane (CP) which also comprises the axis of the main body component 200.

The main body component 200 further comprises a transition portion 205 extending between the distal end of the main body portion 203 and a proximal end of the concaved portion 206. A cross-section of the transition portion 205 evolves from a circular shape towards the proximal end of the transition portion 205 to an elliptical shape towards the distal end of the transition portion 205. A larger diameter of this shape extends in the central plane (CP).

The main body component 200 is formed of a multilayer braided framework 20 made of a plurality of filaments and is devoid of any cover layer. Preferably, the framework 20 comprises a plurality of interconnected layers and each layer is interlaced to form a lattice.

For example, the framework 20 of the main body component 200 is multiple braided as shown in FIG. 26, comprises three layers 21, 22, 23 whose plies are not distinct at the time of braiding, a given number of wires 24 of the plies of the first layer 21 are interlaced with the plies of the second layer 22 and/or of the third layer 23, forming a complex lattice.

Since the multilayer braiding structure provides high friction at the concaved portion 206, the lumen extensions 300 are strongly grasped by the main body component 200. Accordingly, the risk of migration of the lumen extensions 300 is reduced.

More preferably, the framework 20 has, in its deployed state, a configuration wherein an outermost layer 23 applies against the wall 25 of the body lumen (e.g., a vessel) the other layers 21, 22 extending substantially along cylindrical surfaces distinct from the outermost layer 23 so as to assure an improved flow 26 in a branch 27 the inlet of which would be covered by the main body component 200. Thanks to the multiplicity of the layers, the pressure of blood flow passing therethrough drops and results in improved laminated shear flow which leads to permanent branches patency.

Figure 28:
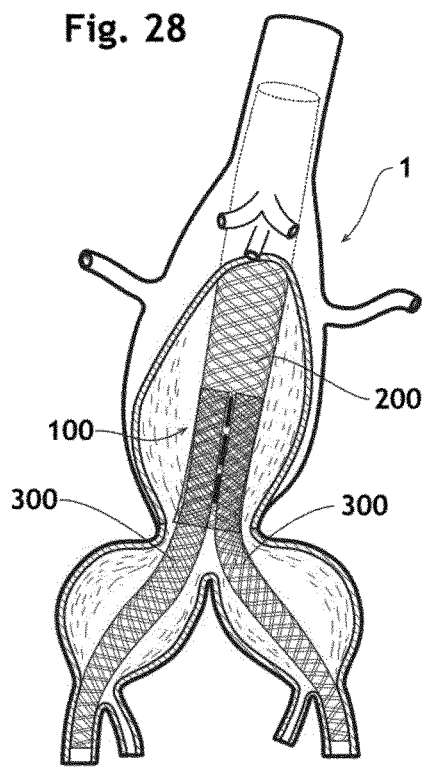
FIG. 28 is a partially cutaway elevation view of a thoracoabdominal bifurcated aneurysm (TABA) and an embodiment of the multi-lumen stent assembly according to the present invention deployed therein.
Figure 30:
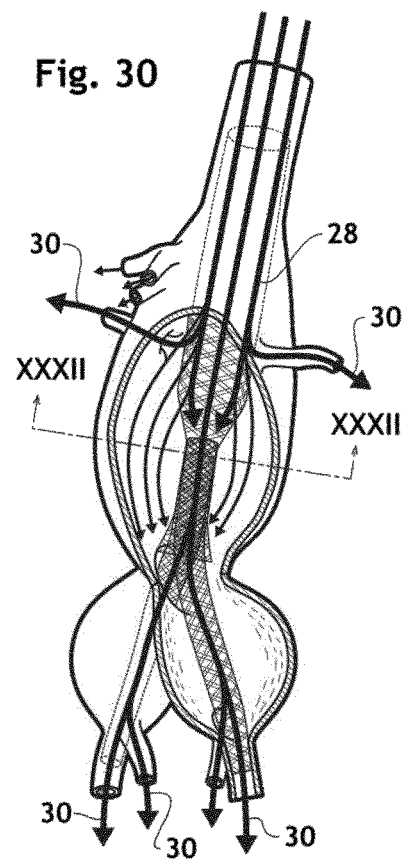
FIG. 30 is a partially cutaway perspective view of the TABA and the multi-lumen assembly shown in FIG. 28.
Figure 34:
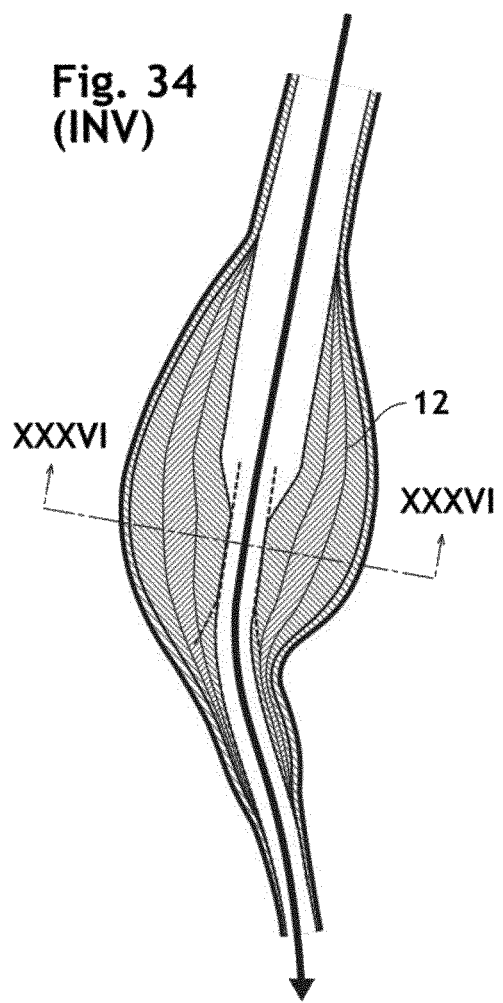
FIG. 34 shows a completely excluded aneurysm by formation of an organized thrombus within the aneurysm shown in FIGS. 28 and 30.

An intersection of the wall of the transition portion 205 by a plane comprising the axis of the main body component 200 and normal to the central plane (CP) defines an angle α with respect to the central plane (CP) as shown in FIG. 20A. Tests carried out with various stent configurations demonstrate that the value of angle α has a non-neglectible influence on the stent's efficiency. Said angle α should better be between at least 10° and at most 55° when the stent assembly 100 is in fully expanded state. Thanks to an optimal value of angle α, the inner layers 21, 22 of the main body component at the transition portion 205 effectively deviates the blood flow 28 towards the centre of the aorta (FIGS. 28 and 30). This results in formation of organised thrombus 12 in the aneurysm, even in the space that was originally the aorta 29 (FIGS. 34 and 36). On the other hand, the branches the inlet of which is covered by the main body component 200 maintain their patency and a blood flow 30 therein as shown in FIG. 30. That means that, without undertaking open surgery, the stent assembly 100 can provide the same effect as replacement of the diseased section with artificial grafts by open surgery. Furthermore, the mechanical structure of the main body component 200 with fully thrombosed aneurysm allows the endothelial cell film to be formed on a wall thereof. The formation of endothelial cell film on the wall of assembly means that the artery is completely cured (excluded).

In order to accelerate the thrombosis of aneurysm, said angle α should be at most 55°, preferably at most 45°, more preferably at most 35°, even more preferably at most 25° with respect to the central plane (CP).

Figure 29:
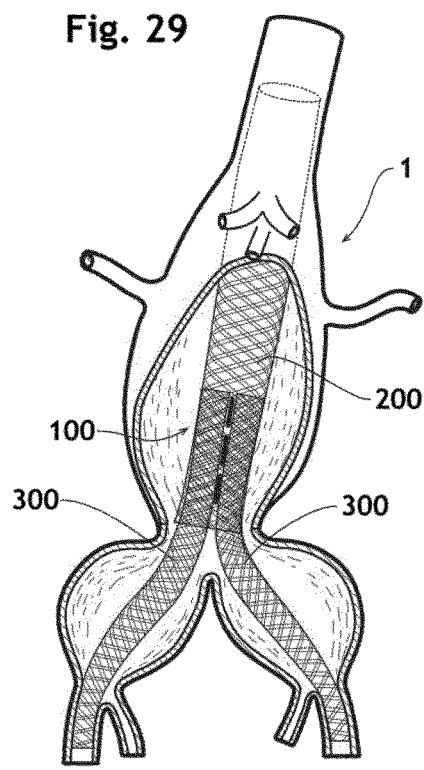
FIG. 29 is a partially cutaway elevation view of a thoracoabdominal bifurcated aneurysm (TABA) and a prosthesis assembly deployed therein.
Figure 31:
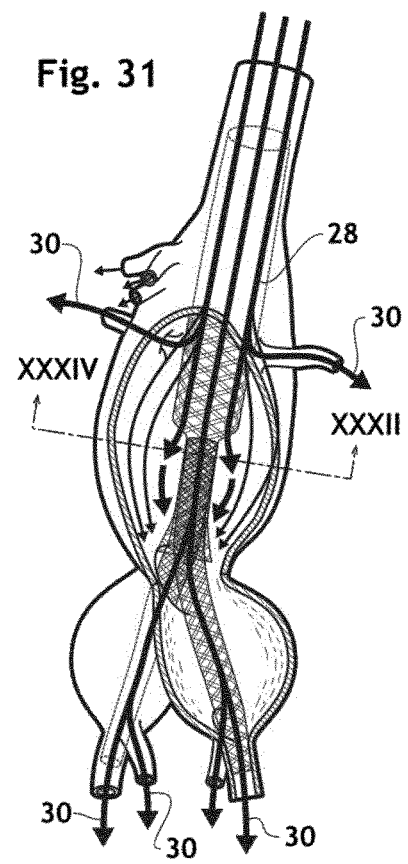
FIG. 31 is a partially cutaway perspective view of the TABA and the prosthesis assembly shown in FIG. 29.
Figure 32:
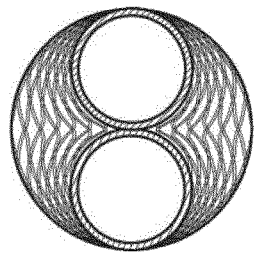
FIG. 32 is a section view of the distal end of the stent assembly shown in FIG. 30 according to a cutting plane XXXII-XXXII of FIG. 30.
Figure 33:
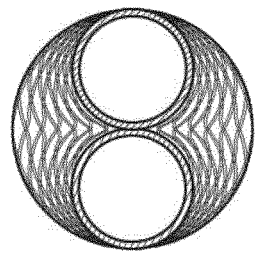
FIG. 33 is a section view of the distal end of the stent assembly shown in FIG. 31 according to a cutting plane XXXIII-XXXIII of FIG. 31.
Figure 35:
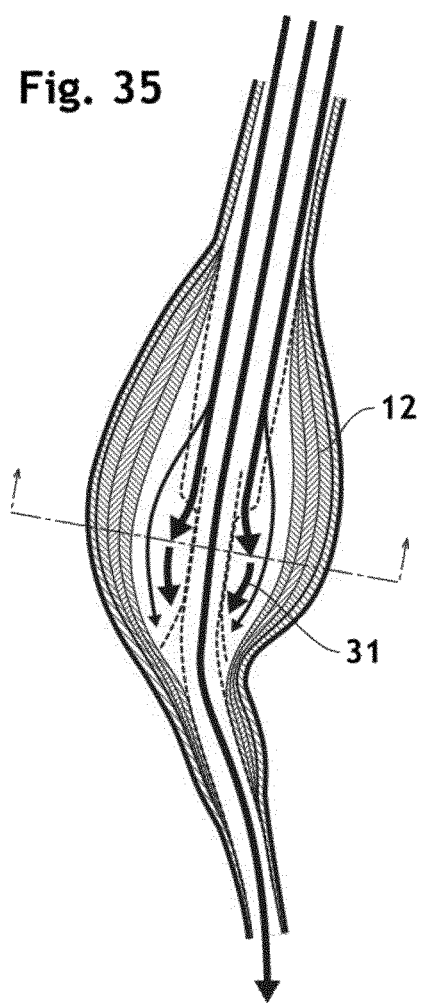
FIG. 35 shows a partial formation of an organized thrombus within the aneurysm shown in FIGS. 29 and 30.

If the angle α is greater than 55°, a sufficient deviation effect of the blood flow 28 on the wall of the transition portion 205 cannot be expected (FIGS. 29 and 31). This provokes an insufficient thrombosis of the aneurysm and a residual blood flow 31 will be observed as shown in FIGS. 35 and 37. The endothelization will not occur on a wall of the main body component 200 where thrombosis is not completed. Therefore, the risks of unexpected growth of aneurysm and undesired restenosis remain. On the other hand, the angle α should be at least 10° in order to obtain a practically handy length of a main body component for delivery, preferably at least 15°, more preferably at least 20°.

When the stent assembly 100 is in a deployed state, the average porosity of the main body portion 203 is preferably at least 50% and at most 75% and the average porosity of the double-barrelled portion 208 is preferably less than the one of the main body portion 203. Less porosity of the double-barrelled portion 208 compared to the one of the main body portion 203 can accelerate the formation of organized thrombus of the aneurysm.

Each lumen extension 300 is preferably a stent devoid of any impermeable layer in order to reduce the risk of undesired expansion or extension of the aneurysm around the lumen extension 300 after implantation of the assembly 100. The lumen extension 300 is preferably formed of a multilayer braided framework made of a plurality of filaments and is devoid of any cover layer. Preferably, the framework comprises a plurality of interconnected layers and each layer is interlaced to form a lattice. More preferably, the framework has a configuration, in its deployed state, an outermost layer applies against the wall of the body lumen (e.g., vessel) the other layers extending substantially along cylindrical surfaces distinct from the outermost layer so as to assure the improved flow in a branch and/or collateral the inlet of which is covered by the lumen extension and to prevent in-stent (re)stenosis.

In fully expanded state, the external diameter of lumen extension 300 is preferably at least 10% and at most 50% greater than the inner diameter of the double-barrelled portion 208 so as to reduce the migration risk of the lumen extension 300 while avoiding applying too much radial force to a wall of the iliac artery. Said external diameter is more preferably at least 13% and at most 20% greater than said inner diameter.

In order to provide a consistent orientation for the devices, systems, and methods, describes herein, the term "proximal" will be used to describe a relation or orientation toward away from the branches of the bifurcated vessel, i.e., toward the heart, and the term "distal" will be used to describe a position or orientation toward the branches of the bifurcated vessel, i.e., toward away from the heart. Therefore, the devices, systems, and methods, can be described as having a proximal component and a distal component.

FIG. 38 shows the targeted site for delivery and implantation of a prosthesis as disclosed above within a thoracoabdominal bifurcated aneurysm 1 (TABA). The proximal end 401 of a deployment catheter 400 for the main body component 200 is glided along a previously positioned first guide wire 402 (not shown) and the main body component 200 is allowed to radially expend in the aorta (FIG. 39) and through a portion of the TABA 1 (FIG. 40). Thanks to sufficient radial forth provided by the multilayer braiding, any additional fastened means between the main body component 200 and the aorta is not required if there is an adequate landing zone at the distal side of the aneurysm.

Figure 41:
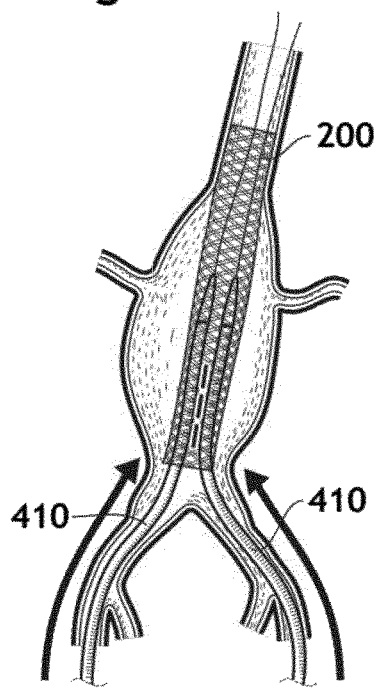
Figure 42:
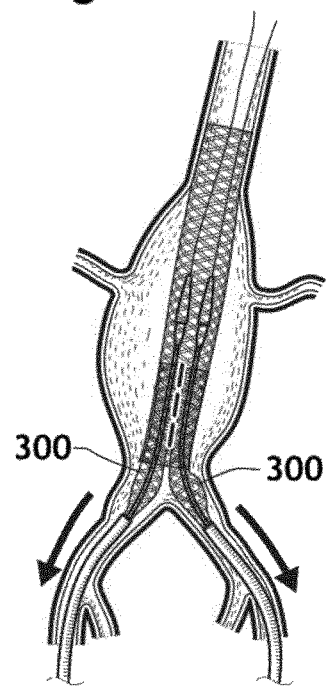
Figure 43:
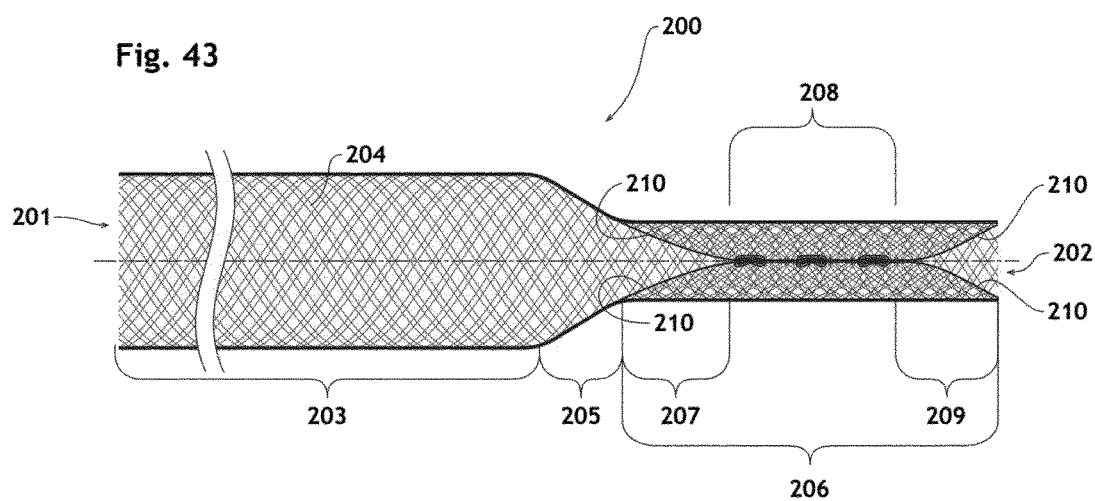
FIG. 43 is a side view of another embodiment of the main body component according to the present invention in fully expanded state.
Figure 44:
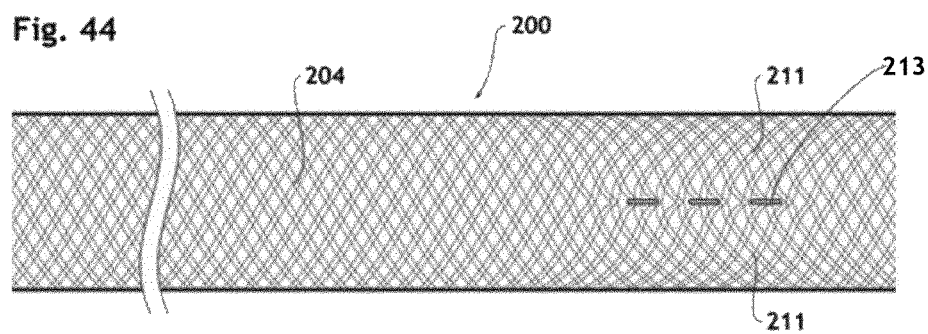
FIG. 44 is an elevation view of the main body component shown in FIG. 43.
Figure 45:
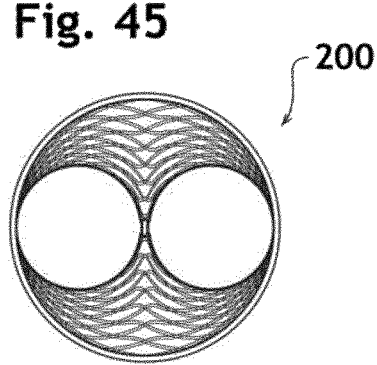
FIG. 45 is a plan view of the main body component shown in FIG. 43.
Figure 46:
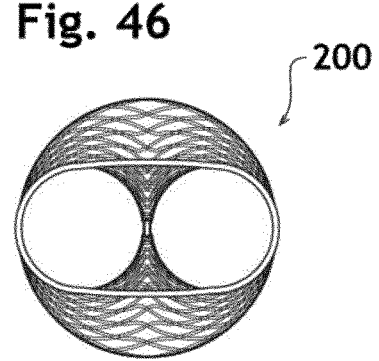
FIG. 46 is a bottom view of the main body component shown in FIG. 43.
Figure 47:
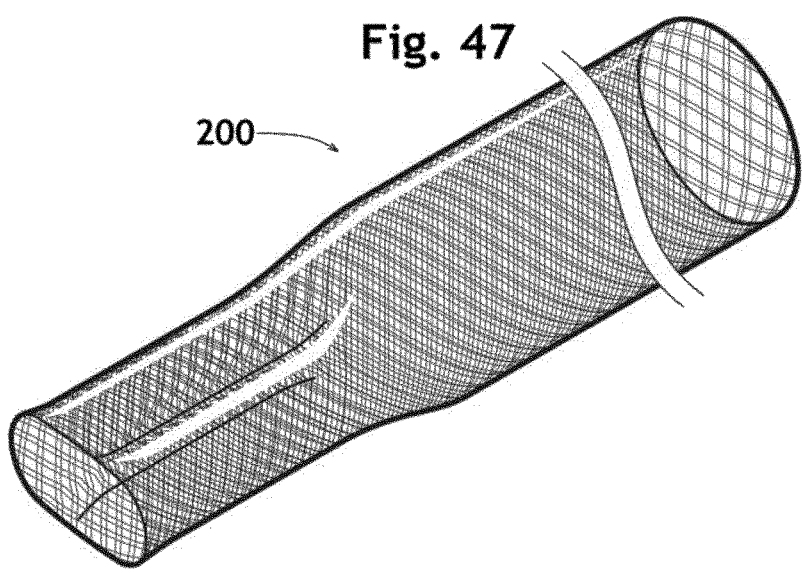
FIG. 47 is a perspective view of the main body component shown in FIG. 43.

FIG. 38 depicts the initial stage of the main body component 200 deployment at the target site. The delivery catheter 400 has a movable outer sheath 402, which overlays the main body component 200. When the outer sheath 402 is pulled distally, the main body component 200 is exposed but may remain in an undeployed configuration until re-sheathing means has been deactivated. Once the re-sheathing means deactivated, the main body component 200 is free to radially expand, thereby enlarging to contact at least a portion of the internal walls of the blood vessel. The assembly deployment process is continued including the deployment of one or two lumen of the lumen extension(s) 300 (FIGS. 41 and 42). In order to reduce the risk of migration of the lumen extensions 300, the lumen extensions 300 should be inserted to be fully overlapped by the concaved portion 206.

FIGS. 43-47 shows another embodiment of a main body component 200 according to the present invention. The concaved portion 206 further comprises a distal portion 209 between the double-barrelled portion 208 and the distal end 202 of the main body component 200. The distance between the two ridges 210 increases toward the distal end 202. This design can make it easier to insert a deployment catheter 410 carrying the lumen extensions 300 into the distal end 202 of the main body component 200.

In an alternative embodiment shown in FIGS. 48-52, the double-barrelled portion 208 of the main body component 200 further comprises, at its distal end, a diverging cone-shaped portion 212. This design can also make it easier to insert the deployment catheter 410 carrying the lumen extensions 300 into the distal end 202 of the main body component 200.

The porosity of the main body portion 203 of the main body component 200 is preferably at least 60% and at greatest 70% so as to have a laminar flow with an ideal velocity in the aneurysm sac and result in acceleration of thrombosis therein. The value of angle β, formed between crossing braided filaments of the double-barrelled portion 208 shown in FIG. 20B, has an influence on the porosity of this portion. Accordingly, when the assembly 100 is deployed, angle β should better be greater than 95°, preferably at least 100° and at greatest 150° so as to obtain a porosity less than 70%.

FIGS. 53 to 57 show a method for manufacturing a main body component 200 for the prosthesis assembly suitable for deployment into a bifurcated vessel according to the present invention.

Figure 53:
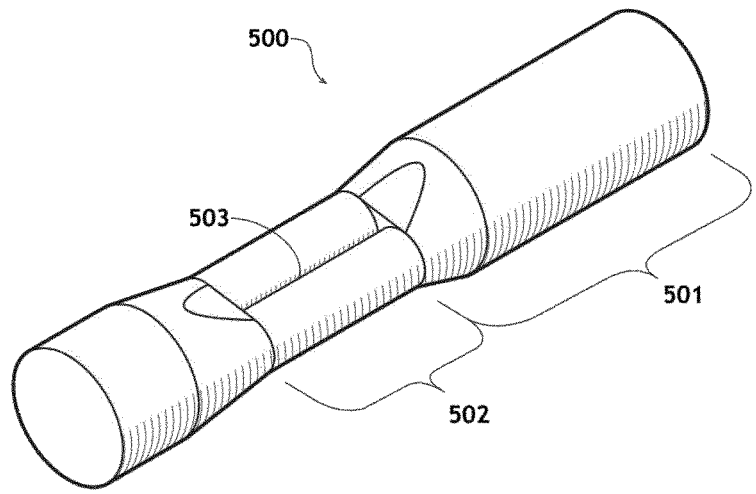
FIG. 53 is a perspective view of a preferred embodiment of a mandrel according to the present invention.

A mandrel 500 shown in FIG. 53 comprises at least one main portion 501 comprising a cylindrical form and two bars 502 connected to a distal end of the main portion 501. The two bars 502 have a cylindrical form and are disposed parallel to each other. The diameters of the two bars 502 are smaller than the diameter of the main portion 501. A linear space 503 extends between the two bars 502 along the longitudinal axis of the mandrel 500.

Metal filaments are bundled at an end of the mandrel 500 and fixed with a fixing means 504. The material for the metal filaments may be selected from a group of cobalt-chromium alloy such as Phynox® and Elgiloy, titanium, and titanium alloy such as Nitinol®.

Figure 55:
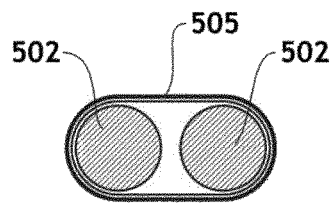
FIG. 55 is a cross-section of the mandrel and the multilayer braided framework shown in FIG. 54 according to a cutting plane LV-LV of FIG. 54.
Figure 54:
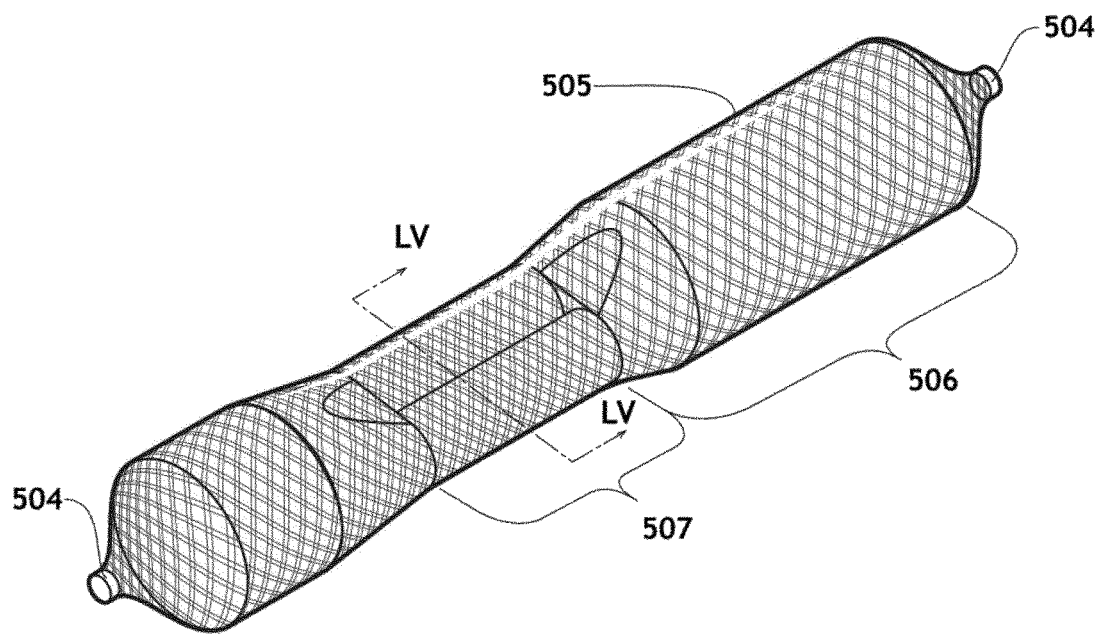
FIG. 54 is a perspective view of the mandrel shown in FIG. 53 surrounded with a multilayer braided framework according to the present invention.
Figure 57:
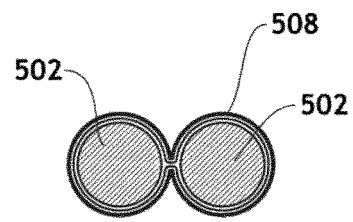
FIG. 57 is a cross-section of the mandrel and the partially concaved multilayer braided framework shown in FIG. 56 according to a cutting plane LVII-LVII of FIG. 56.
Figure 56:
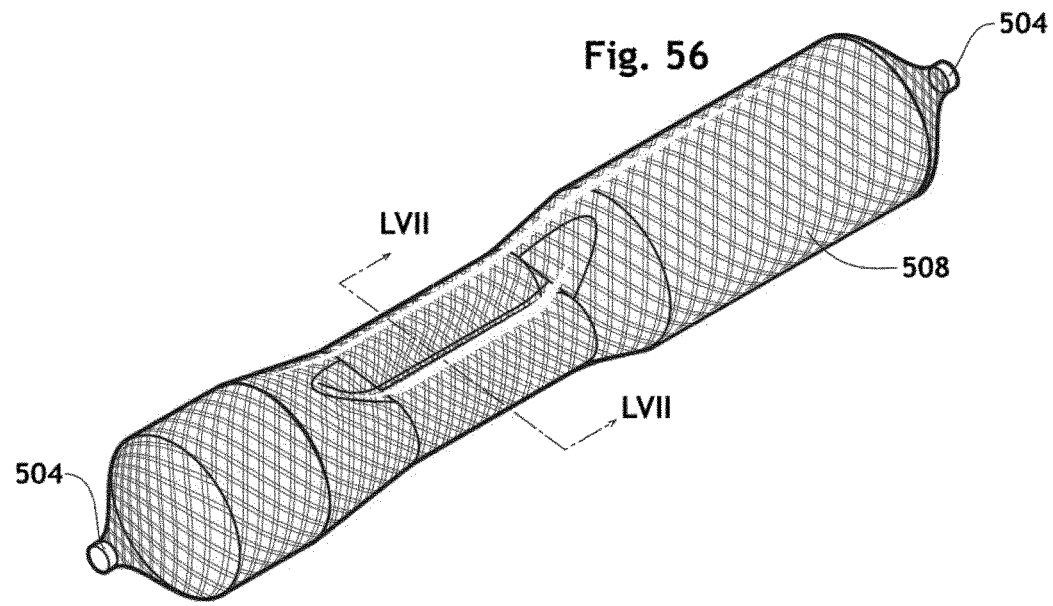
FIG. 56 is a perspective view of the mandrel shown in FIGS. 53 and 54 and a partially concaved multilayer braided framework.

A braided framework 505 is formed around the mandrel 500 with the metal filaments (FIGS. 54 and 55). The braided framework 505 should comprise at least one main portion 506 having cylindrical form and at least one flattened portion 507 having an oval cross-section. The braided metal filaments 505 are bundled and fixed with a fixing means 504 at the other end of the mandrel 500. The mandrel 500 and surrounding braided framework 505 are put into a tube or bag and subjected to an external pressure so as to create a concaved shape in the flatten portion 507 along the linear space 503 of the mandrel 500. The external pressure is preferably hydraulic. The concaved framework 508 is further subjected to a thermal treatment so as to memorize the concaved shape (by imparting a phase transition to the metal). Both ends of the thermal treated framework are cut off at desired length and the mandrel 500 is removed from inside of the thermal treated framework 509.

Figure 58:
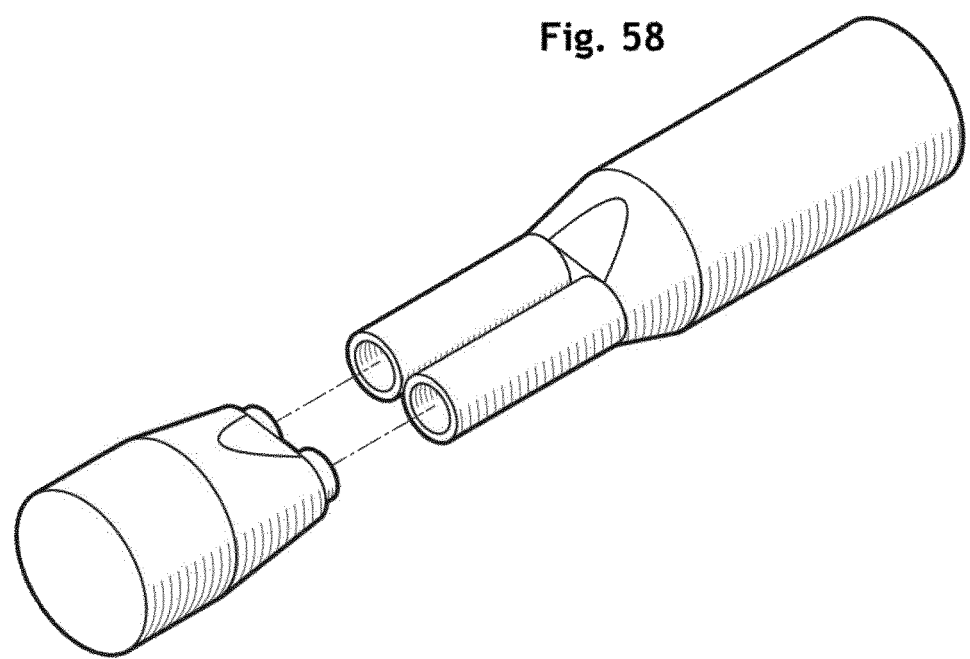
FIG. 58 is a perspective view of the mandrel shown in FIG. 53 in two separated parts.
Figure 59:
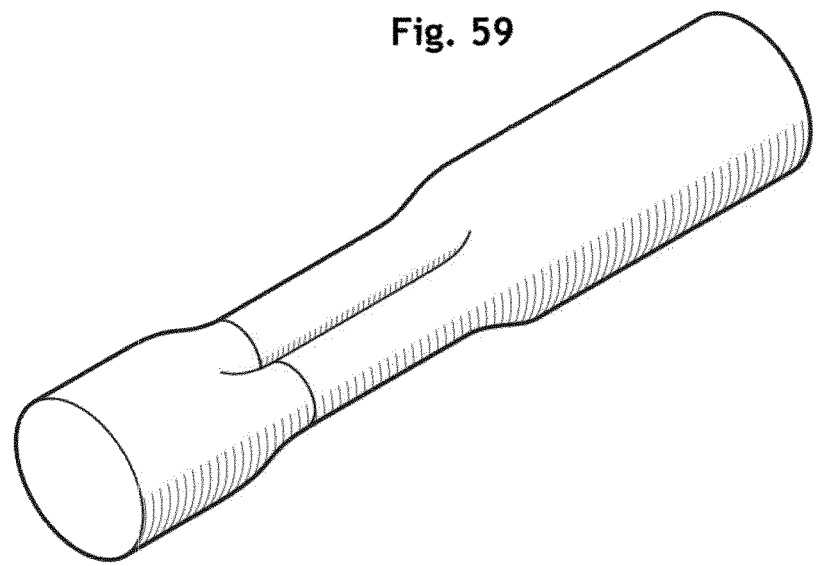
FIGS. 59 and 60 are a perspective view of another embodiment of a mandrel according to the present invention.
Figure 60:
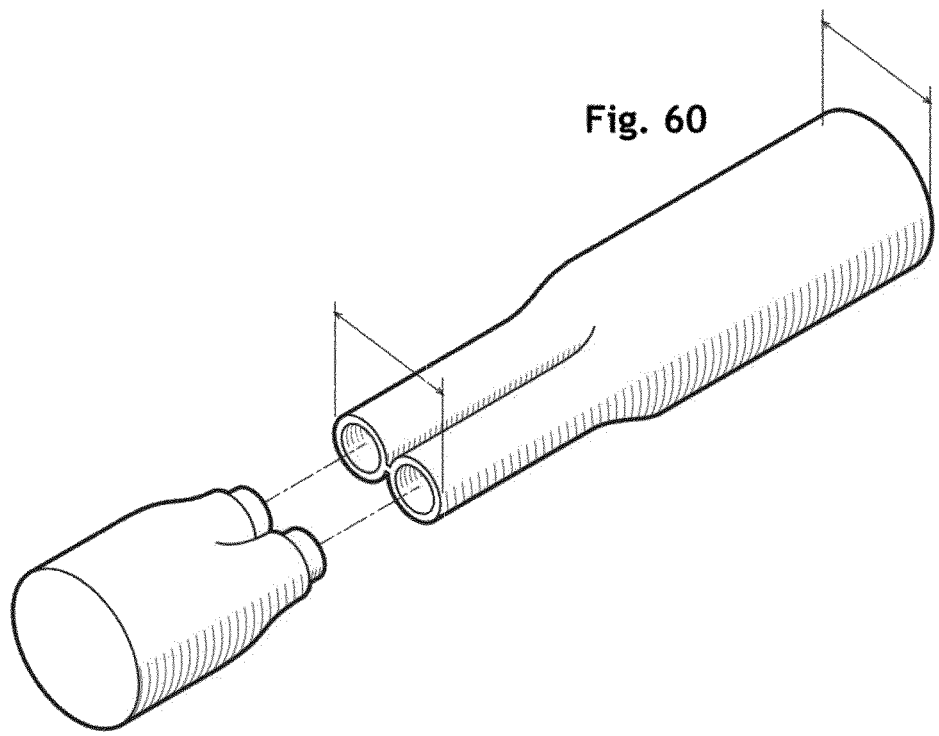

The mandrel 500 is preferably made of at least two parts which are detachable from each other so as to allow removing the concaved framework from the mandrel 508 without deformation (FIG. 58). The mandrel 500 can comprise two sets, or more than two, of configuration comprising one main portion 501 and two bars 502, so as to allow manufacturing a plurality of main body components 200 at once. An alternative embodiment of the mandrel is depicted in FIGS. 59 and 60.

By selecting judicious combinations of main body components 200 and the corresponding lumen extensions 300, various configurations of the stent assembly according to the present invention can be made available without necessity to manufacture custom-made elements to fit each patient's anatomy like fenestrated and branching stent-grafts requiring. The manufacturing method is quite simple and it can save time to provide an adequate assembly to patient as soon as a dangerous aneurysm is detected.

EXAMPLES

Example 1: Simulation In Vitro

Relative velocity of the blood flow passing through a wall of main body component according to the present invention and entering into an aneurysmal sac is simulated in 2D with a vertical slice of the main body component.

Figure 61:
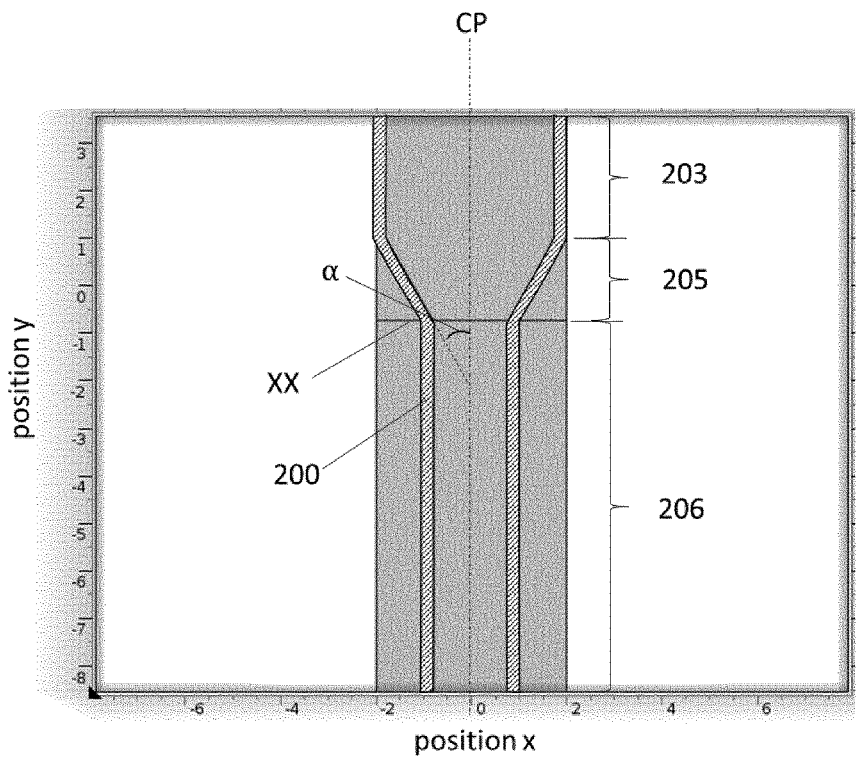
FIG. 61 shows a simulated main body component according to present invention in 2D.
Figure 62:
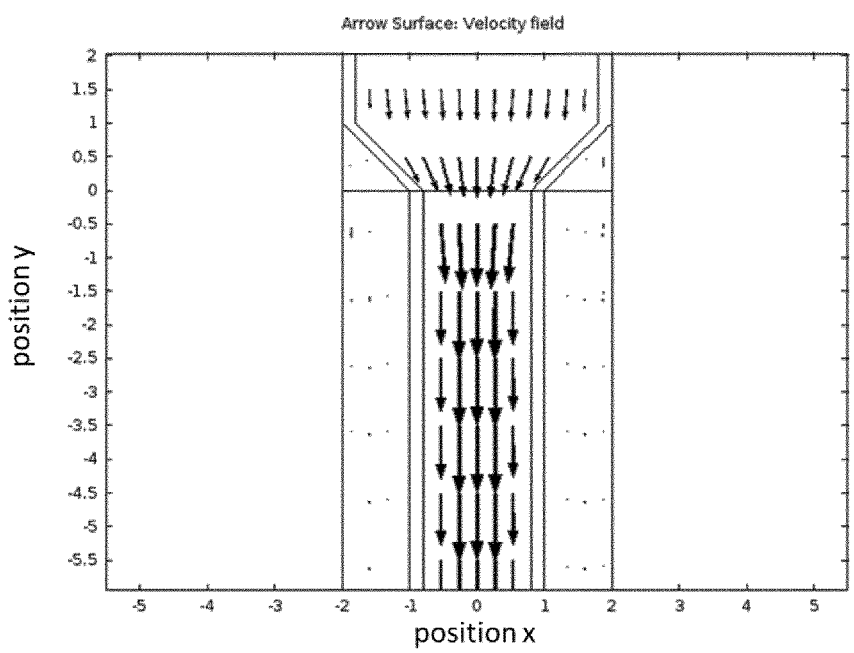
FIG. 62 shows a surface velocity simulated for the main body component showed in FIG. 61.

As shown in FIG. 61, the main body component 200 was considered as an equivalent thick porous medium with homogenous material proprieties. The geometry of the simulated main body component 200 can be divided in three part: the top one bigger (203, i.e., a main body portion), the bottom one smaller (206, i.e., a concaved portion) and the region unites them (205, i.e., a transitional portion). 11 times of simulation have been run with different values of angle α (10°, 15°, 20°, 25°, 30°, 35°, 40°, 45°, 50°, 55° and 60°) which is defined with a wall of the transitional portion 205 and the central plane (CP) as defined in the Detailed Description of the invention. For example, the behaviour of the velocity for the case with 45° of angle α is shown in FIG. 62.

Figure 63:
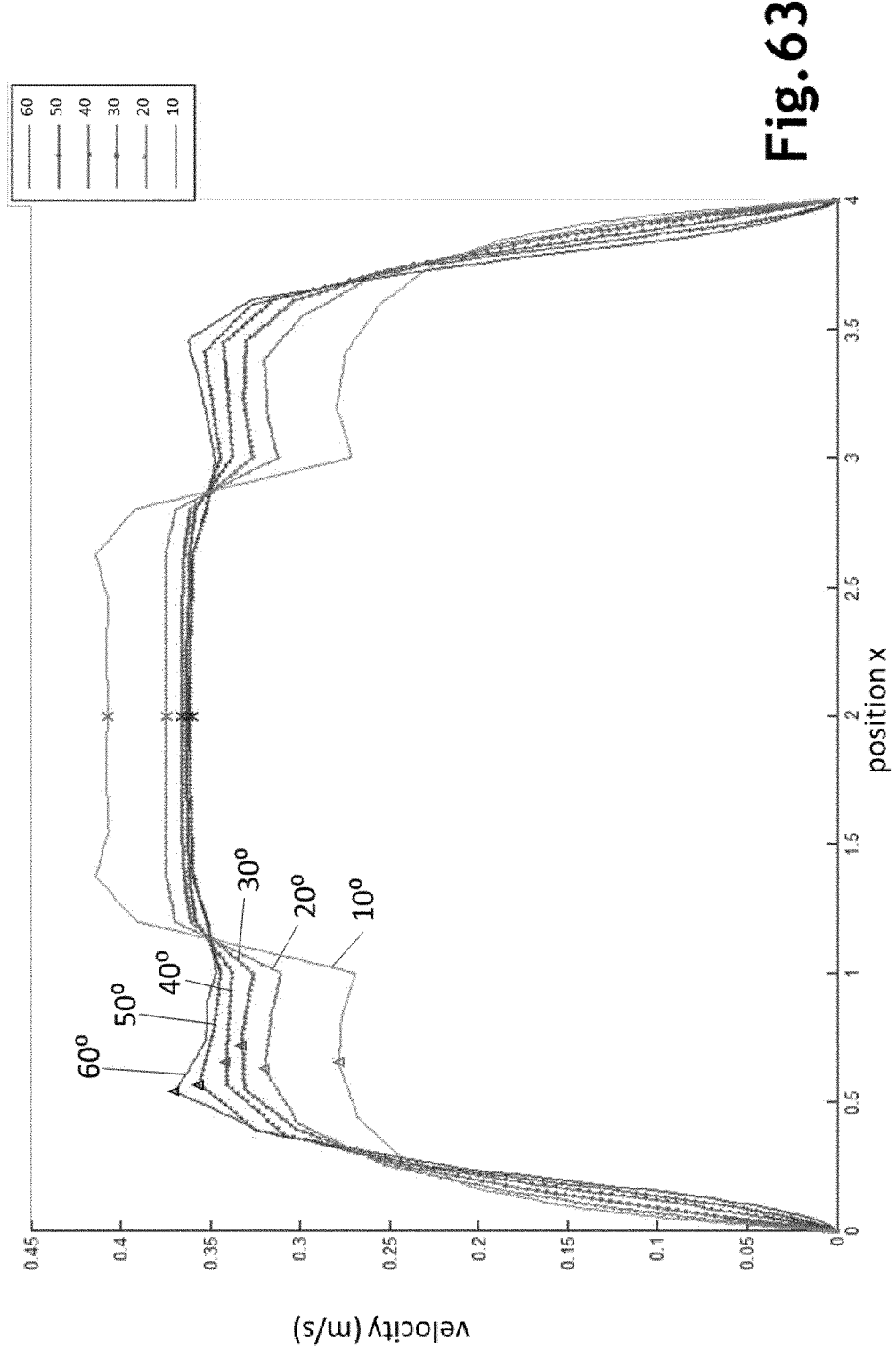
FIG. 63 shows plots of velocities along a black line XX shown in FIG. 61 for the various angle α.
Figure 64:
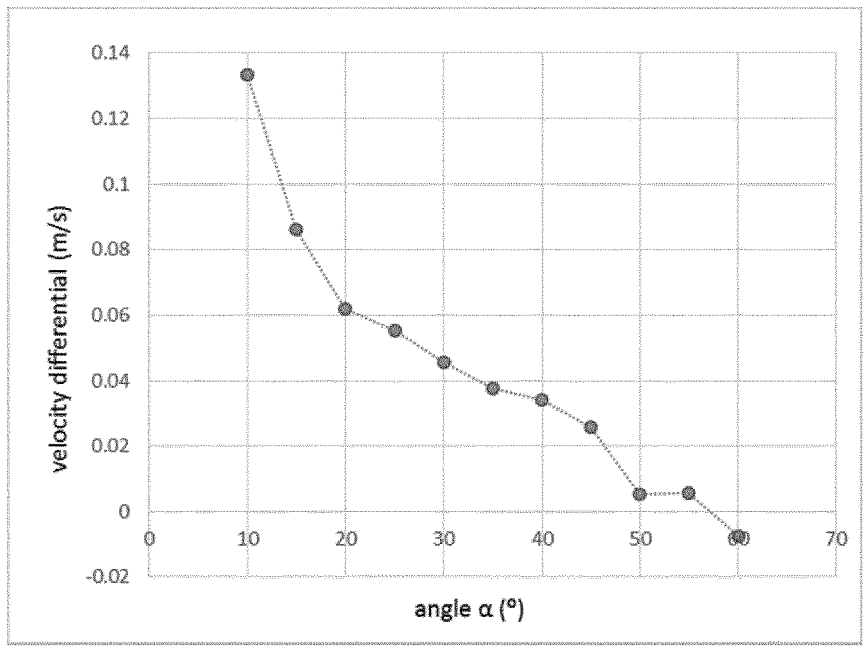
FIG. 64 shows absolute difference (m/s) between the velocity (-*-) at the centre of the geometry and the peak velocity (-▲-) in the left external part for each angle α shown in FIG. 63.
Figure 65:
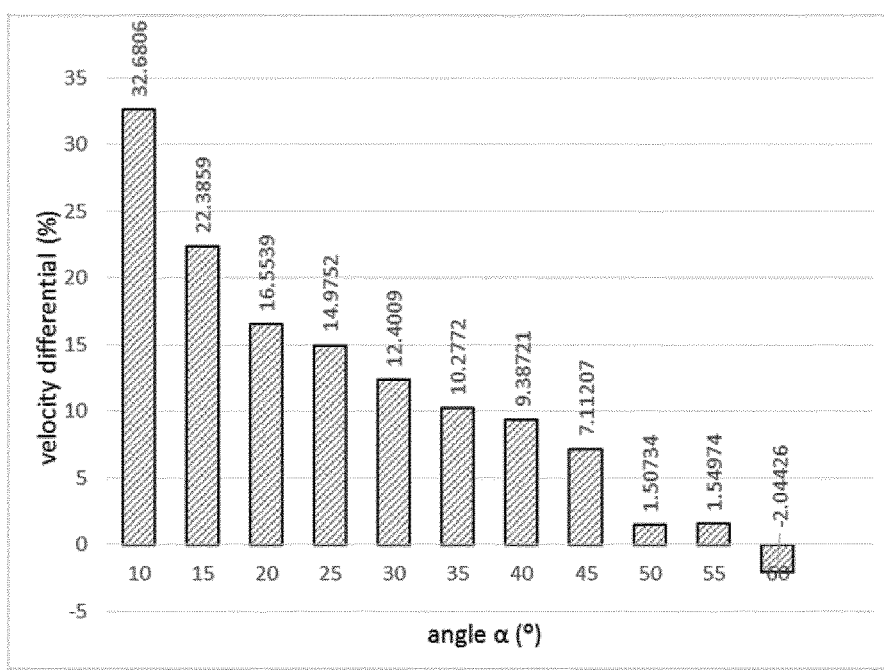
FIG. 65 shows velocity difference in percentage (%) between the velocity (-*-) at the centre of the geometry and the peak velocity (-▲-) in the left external part, for each angle α shown in FIG. 63.

FIG. 63 shows plots of velocities along a black line XX shown in FIG. 61 for the various angle α. FIG. 64 shows absolute difference (m/s) between the velocity (-*-) at the centre of the geometry (namely, the velocity of blood flow staying within the main body component) and the peak velocity (-▲-) in the left external part for each angle α (namely, the velocity of blood flow outside of the main body component). FIG. 65 shows said difference in percentage (%). Velocity differentials simulated for various values of angle α are summarized in Table 1.

TABLE 1

Velocity differentials simulated for various values of angle α

| Angle α (°) | velocity differential (m/s) | velocity differential (%) |
| --- | --- | --- |
| 10 | 0.13321 | 32.6806 |
| 15 | 0.086077 | 22.3859 |
| 20 | 0.061989 | 16.5539 |
| 25 | 0.055215 | 14.9752 |
| 30 | 0.045383 | 12.4009 |
| 35 | 0.037454 | 10.2772 |
| 40 | 0.034135 | 9.38721 |
| 45 | 0.025784 | 7.11207 |
| 50 | 0.0054513 | 1.50734 |
| 55 | 0.0055982 | 1.54974 |
| 60 | −0.007397 | −2.04426 |

Surprisingly, relative velocity of blood flow outside the main body component to the one inside thereof was greatly affected with the value of angle α. When the angle α is 60°, the outside velocity is greater than the inside velocity (i.e., velocity differential=−2.0446%). That means that, even if the blood flow is laminated by passing through the wall of the main body component, since the outside velocity is relatively great, it will prevent from the desired formation of organized thrombus in the aneurysm. On the other hand, when the angle α is 55°, the outside velocity is start to smaller than the inside velocity (i.e., velocity differential=+1.54974%). That means that the formation of organized thrombus can be expected. Therefore, 55° can be considered as "inflection point". When the angle α is 45°, the difference became more than four times of the one with 55° and when it was 25°, the difference was almost 10 times greater than the one with 55°. The greater the difference in velocity, the faster the formation of organized thrombus can be expected.

Example 2: Clinical Cases

The details of the stent assembly according to the present invention used for primary clinical cases to treat the thoracoabdominal bifurcated aneurysm (TABA) are indicated below.

The main body component used for the clinical cases was made of 116 of cobalt alloy (200-240 micron in diameter) and had three interlaced layers. The length of the main body component was 150 mm and the diameter of the main body portion was 32 mm in its fully expanded state. The angle α was 25° in fully expanded state. The length of the concaved line was 32 mm. The lumen extensions were made by 80 of cobalt alloy (100-120 micron in diameter) and had three interlaced layers. The length of the extension lumen was 120 mm and the diameter of the extension lumen was 16 mm in its fully expanded state. Therefore, the external diameter of lumen extension is 14% greater than the inner diameter of the double-barrelled portion.

The prosthesis assembly was implanted to a patient who had the thoracoabdominal bifurcated aneurysm (TABA). The progress of organized thrombus of aneurysm was assessed with CT-scan images taken respectively before implantation (FIG. 66), 1 month (FIG. 67) and 2 months (FIG. 68) after the implantation.

Surprisingly a complete organized thrombus of aneurysm was observed 6 months after the implantation. On the other hand, the collaterals the inlet of which was completely covered by the main body component maintained their patency (FIG. 69). Furthermore, the mechanical structure of the main body component with fully thrombosed aneurysm allowed an endothelial cell film to be formed. The formation of endothelial cell film on the wall of assembly means that the aneurysm is completely cured (excluded).

The invention claimed is:

1. A multi-lumen stent assembly suitable for deployment in a bifurcated vessel comprising a main vessel and at least two branches, said assembly comprising:
   (i) a self-expandable main body component able to expand from a radially compressed state in a delivery configuration to a radially expanded state, the main body component extending along an axis and having a proximal end configured to extend away from the at least two branches of the bifurcated vessel and a distal end configured to extend toward the at least two branches of the bifurcated vessel, the main body component comprising:
      at the proximal end of the main body component, a main body portion comprising a lumen in a cylindrical form with a circular cross-section and a constant diameter;
      a transition portion extending distally from a distal end of the main body portion, a cross-section of the transition portion evolving from a circular shape towards a proximal end of the transition portion to an elliptical shape towards a distal end of the transition portion; and
      a flattened portion extending distally from the transition portion distal end towards the main body component distal end, the flattened portion comprising a double-barreled portion, the flattened portion extending along the axis of the main body component, middle lines of the flattened portion defining two opposing ridges within an interior of the flattened portion, a portion of each ridge contacting a portion of the other ridge, the two opposing ridges defining two lumens of the double-barreled portion, each of the two lumens extending along a lumen axis, the lumen axes of the two lumens defining a central plane (CP) which also comprises the axis of the main body component; and
   (ii) two lumen extensions, each lumen extension comprising a tip portion able to be inserted into one of the two lumens of the double-barreled portion from the distal end of the main body component;
   wherein:
      the main body component is formed of a multilayer braiding with a plurality of filaments and is devoid of any cover layer, and is formed of an interconnected multilayer braiding;
      a larger diameter of the transition portion elliptical shape is in the CP;
      an intersection of a wall of the transition portion by a plane comprising the axis of the main body component and normal to the CP defining an angle (a) with respect to the CP, said angle (a) being comprised between at least 10° and at most 55° when the stent assembly is in a deployed state; and
      the flattened portion further comprises a distal portion wherein a distance between the two opposing ridges increases toward the distal end of the main body component.

2. A stent assembly according to claim 1, wherein a porosity of the main body portion is at least 50% and at most 75%, wherein a porosity of the double-barreled portion being less than the porosity of the main body portion, when the stent assembly is in the deployed state.

3. A stent assembly according to claim 2, wherein the porosity of the main body portion is at least 60% and at greatest 70% in the deployed state.

4. A stent assembly according to claim 1, wherein said angle (a) is at least 15°, and at most 55° with respect to the CP.

5. A stent assembly according to claim 1, wherein, when the prosthesis assembly is in the deployed state, a second angle formed between crossing braided filaments of the double-barreled portion is greater than 95°.

6. A stent assembly according to claim 1, wherein each lumen extension is a stent devoid of any impermeable layer.

7. A stent assembly according to claim 6, wherein each lumen extension is formed of a multilayer braided framework made of a plurality of filaments.

8. A stent assembly according to claim 7, wherein the multilayer braided framework comprises a plurality of interconnected layers and each layer is interlaced to form a lattice.

9. A stent assembly according to claim 8, wherein the plurality of interconnected layers of the multilayer braided framework comprises:
   an outermost layer having a cylindrical surface; and
   other layers, and
wherein, in its deployed state, the outermost layer of the framework applies against the wall of the main body component and the other layers extend along cylindrical surfaces distinct from the outermost layer.

10. A stent assembly according to claim 6, wherein, in a fully expanded state, an external diameter of each lumen extension is at least 10% and at most 50% greater than an inner diameter of the double-barreled portion.

11. A stent assembly according to claim 10, wherein, in the fully expanded state, the external diameter of each lumen extension is at least 13% and at most 20% greater than said inner diameter of the double-barreled portion.

* * * * *